United States Patent
Otani et al.

(10) Patent No.: US 10,533,070 B2
(45) Date of Patent: Jan. 14, 2020

(54) FLUORINE ATOM-CONTAINING POLYMER AND USE OF SAME

(71) Applicant: NISSAN CHEMICAL INDUSTRIES, LTD., Tokyo (JP)

(72) Inventors: Naoki Otani, Funabashi (JP); Hirofumi Ota, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 183 days.

(21) Appl. No.: 15/553,836

(22) PCT Filed: Feb. 5, 2016

(86) PCT No.: PCT/JP2016/053447
§ 371 (c)(1),
(2) Date: Aug. 25, 2017

(87) PCT Pub. No.: WO2016/136425
PCT Pub. Date: Sep. 1, 2016

(65) Prior Publication Data
US 2018/0030200 A1 Feb. 1, 2018

(30) Foreign Application Priority Data

Feb. 27, 2015 (JP) .................. 2015-038272

(51) Int. Cl.
| | | |
|---|---|---|
| C09K 11/06 | (2006.01) | |
| C08G 61/12 | (2006.01) | |
| C07C 217/76 | (2006.01) | |
| C07F 5/02 | (2006.01) | |
| C07C 25/22 | (2006.01) | |

(52) U.S. Cl.
CPC ............. C08G 61/12 (2013.01); C07C 25/22 (2013.01); C07C 217/76 (2013.01); C07F 5/02 (2013.01); C09K 11/06 (2013.01); C08G 2261/146 (2013.01); C08G 2261/1424 (2013.01); C08G 2261/19 (2013.01); C08G 2261/3142 (2013.01); C08G 2261/3162 (2013.01); C08G 2261/3424 (2013.01); C08G 2261/411 (2013.01); C08G 2261/512 (2013.01); C08G 2261/95 (2013.01)

(58) Field of Classification Search
None
See application file for complete search history.

(56) References Cited

U.S. PATENT DOCUMENTS

| | | |
|---|---|---|
| 2007/0031699 A1 | 2/2007 | Yamada et al. |
| 2013/0270544 A1 | 10/2013 | Anryu et al. |
| 2013/0306950 A1 | 11/2013 | Middleton |
| 2017/0133589 A1 | 5/2017 | Ota et al. |
| 2017/0200897 A1 | 7/2017 | Otani et al. |

FOREIGN PATENT DOCUMENTS

| | | | |
|---|---|---|---|
| CN | 101671256 A | 3/2010 | |
| JP | 2009-96782 A | 5/2009 | |
| JP | 2009-139214 A | 6/2009 | |
| JP | 2014-505144 A | 2/2014 | |
| JP | 2014-224101 A | 12/2014 | |
| WO | WO-02051958 A1 * | 7/2002 | .......... H01L 51/002 |
| WO | WO 2005/042621 A1 | 5/2005 | |
| WO | WO 2013/006478 A1 | 1/2013 | |
| WO | WO 2015/146912 A1 | 10/2015 | |
| WO | WO 2016/006674 A1 | 1/2016 | |

OTHER PUBLICATIONS

Liu et al. "Stable Superhydrophobic Fluorine Containing Polyfluorenes" Chinese Journal of Polymer Science, 30(2), 2012, 308-315. (Year: 2012).*

(Continued)

*Primary Examiner* — Robert S Loewe
(74) *Attorney, Agent, or Firm* — Birch, Stewart, Kolasch & Birch, LLP

(57) ABSTRACT

Provided is a fluorine atom-containing polymer which is a condensation polymer of a fluorene derivative that provides a repeating unit represented by formula (1), a fluorene derivative that provides a repeating unit represented by formula (2) and a fluorene derivative that provides a repeating unit represented by formula (3).

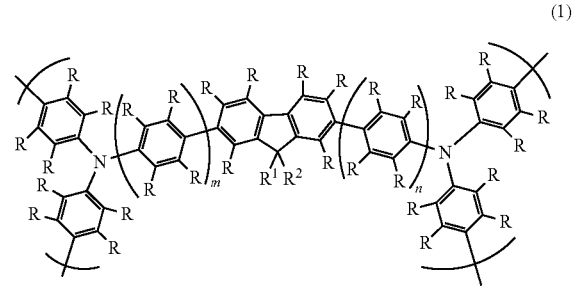

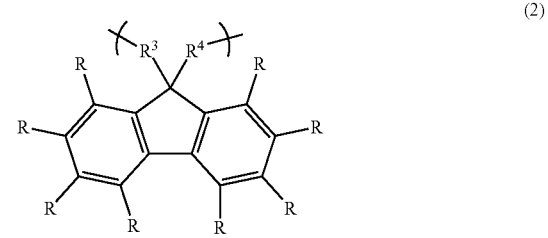

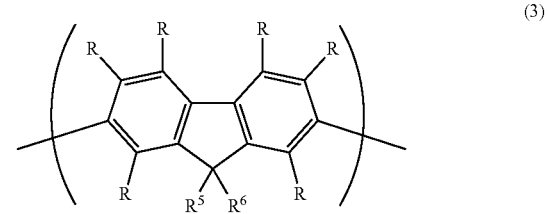

16 Claims, 1 Drawing Sheet

(56) References Cited

OTHER PUBLICATIONS

Extended European Search Report dated Jan. 11, 2019, in European Patent Application No. 16755174.6.
Adachi et al., "Electroluminescence in Organic Films with Three-Layer Structure", Japanese Journal of Applied Physics, vol. 27, No. 2, Feb. 1988, pp. L269-L271.
Chen et al., "Light-Emitting Organic Materials with Variable Charge Injection and Transport Properties", Chemistry of Materials, vol. 18, 2006, pp. 204-213.
International Search Report for PCT/JP2016/053447 (PCT/ISA/210) dated Mar. 29, 2016.
Written Opinion of the International Searching Authority for PCT/JP2016/053447 (PCT/ISA/237) dated Mar. 29, 2016.
English Abstract of TW 201231618 A (Aug. 1, 2012).
Office Action dated Apr. 18, 2019, in Taiwan Patent Application No. 105105305.

\* cited by examiner

FLUORINE ATOM-CONTAINING POLYMER AND USE OF SAME

TECHNICAL FIELD

The present invention relates to a fluorine atom-containing polymer and its use.

BACKGROUND ART

Charge-transporting thin films are used in organic electroluminescent (EL) devices. Methods of forming such charge-transporting thin films are broadly divided into dry processes such as vapor deposition and wet processes such as spin coating. These processes are selectively used as appropriate according to the surface area of the thin film to be formed and the solubility in organic solvents of the substance to be rendered into a thin film.

In general, between the anode and the light-emitting layer of an organic EL device, there are two layers—one called the hole-injecting layer and another called the hole-transporting layer—arranged in this order from the anode side. By providing two such layers, efficient charge transport is possible, enabling an organic EL device having high brightness characteristics to be obtained (see, for example, Non-Patent Document 1). Yet, on the other hand, organic EL device production processes also have the drawback that independent steps are normally required to form these respective layers.

Recently, in the field of electronic devices, in order to efficiently manufacture devices at a high yield, there has existed a desire for process simplification and greater simplicity in the device structure. In particular, by replacing a functional multilayer film obtained by stacking a plurality of films in the device with a single-layer film, not only can the manufacturing process be simplified, it is also possible to directly simplify the device structure. Hence, in connection with various electronic devices, there exists a desire for materials capable of producing functional single-layer films that can be substituted for existing functional multilayer films. In the field of organic EL devices as well, there is a growing desire for materials that can replace a functional multilayer film typically composed of a hole-injecting layer and a hole-transporting layer with a single-layer film.

PRIOR ART DOCUMENTS

Non-Patent Documents

Non-Patent Document 1: Adachi, C. et al., *Jpn J. Appl. Phys.*, 27(2), pp. L269-271 (1988)

SUMMARY OF THE INVENTION

Problems to be Solved by the Invention

It is therefore an object of this invention to provide a thin film-forming material which, even when used as a single layer between an anode and a light-emitting layer in a form that contacts both, enables an organic EL device having excellent brightness characteristics to be achieved.

Means for Solving the Problems

The inventors have conducted extensive investigations, as a result of which they have discovered that certain fluorine atom-containing polymers have an excellent solubility in organic solvents, and that a thin film obtained from a charge-transporting varnish containing a charge-transporting substance consisting of this fluorine atom-containing polymer, a charge-transporting substance that contains no fluorine atoms, a dopant consisting of a heteropolyacid, and an organic solvent, even when used as a single layer between an anode and a light-emitting layer in a form that contacts both, gives an organic EL device having excellent brightness characteristics.

Accordingly, the invention provides the following fluorine atom-containing polymer and uses thereof.

1. A fluorine atom-containing polymer which is a condensation polymer of a fluorene derivative that provides recurring units of formula (1) below, a fluorene derivative that provides recurring units of formula (2) below and a fluorene derivative that provides recurring units of formula (3) below

[Chemical Formula 1]

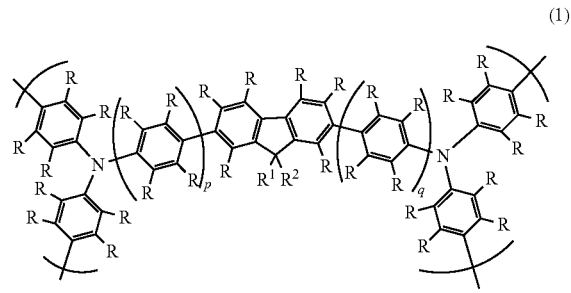

(1)

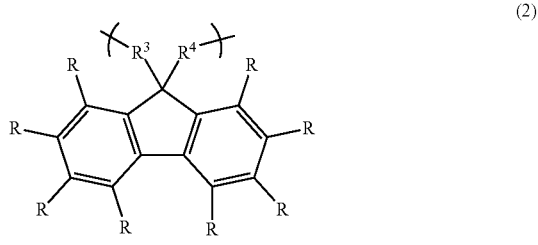

(2)

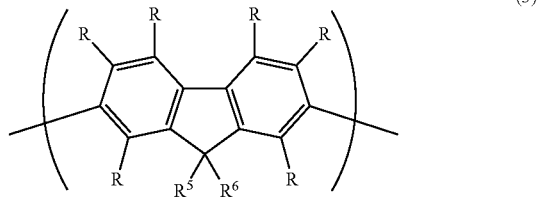

(3)

wherein $R^1$ and $R^2$ are each independently a hydrogen atom, an alkyl group of 1 to 20 carbon atoms, an alkenyl group of 2 to 20 carbon atoms, an alkynyl group of 2 to 20 carbon atoms, an aryl group of 6 to 20 carbon atoms, a heteroaryl group of 2 to 20 carbon atoms, an alkoxy group of 1 to 20 carbon atoms, an alkenyloxy group of 2 to 20 carbon atoms, an alkynyloxy group of 2 to 20 carbon atoms, an aryloxy group of 6 to 20 carbon atoms, a heteroaryloxy group of 2 to 20 carbon atoms or an alkyl group of 2 to 20 carbon atoms which includes at least one ether structure, with the proviso that at least one of $R^1$ and $R^2$ is such an alkyl group, alkoxy group, alkenyloxy group, alkynyloxy group, aryloxy group, heteroaryloxy group, or alkyl group which includes at least one ether structure;

$R^3$ and $R^4$ are each independently a nonconjugated divalent organic group;

$R^5$ is a hydrogen atom, or an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom may be substituted with a fluorine atom;

$R^6$ is an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom is substituted with a fluorine atom;

each R is independently a hydrogen atom, a halogen atom, a nitro group, a cyano group, an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms or alkynyloxy group of 2 to 20 carbon atoms which may be substituted with $Z^1$, or an aryl group of 6 to 20 carbon atoms, heteroaryl group of 2 to 20 carbon atoms, aryloxy group of 6 to 20 carbon atoms or heteroaryloxy group of 2 to 20 carbon atoms which may be substituted with $Z^2$;

$Z^1$ is a halogen atom, a nitro group, a cyano group, or an aryl group of 6 to 20 carbon atoms, heteroaryl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms or heteroaryl group of 2 to 20 carbon atoms which may be substituted with Z;

$Z^2$ is a halogen atom, a nitro group, a cyano group, or an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms or heteroaryl group of 2 to 20 carbon atoms which may be substituted with $Z^3$;

$Z^3$ is a halogen atom, a nitro group or a cyano group; and p and q are each independently 0 or 1.

2. The polymer of 1 above, wherein the weight-average molecular weight is from 1,000 to 200,000.

3. The polymer of 1 or 2 above, wherein $R^1$ and $R^2$ are both alkyl groups of 1 to 20 carbon atoms or both alkyl groups of 2 to 20 carbon atoms which include at least one ether structure.

4. The polymer of any of 1 to 3 above, wherein $R^3$ and $R^4$ are each —$R^c$—Ar— wherein $R^c$ is an alkylene group of 1 to 20 carbon atoms, and Ar is an arylene group of 6 to 20 carbon atoms.

5. The polymer of any of 1 to 4 above, wherein $R^5$ is an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom is substituted with a fluorine atom.

6. A charge-transporting substance consisting of the polymer of any of 1 to 5 above.

7. A charge-transporting varnish comprising the charge-transporting substance of 6 above, a charge-transporting substance that contains no fluorine atoms, a dopant consisting of a heteropolyacid, and an organic solvent.

8. The charge-transporting varnish of 7 above, wherein the charge-transporting substance that contains no fluorine atoms is an aniline derivative.

9. A charge-transporting thin film produced using the charge-transporting varnish of 7 or 8 above.

10. An electronic device comprising the charge-transporting thin film of 9 above.

11. An organic electroluminescent device comprising the charge-transporting thin film of 9 above.

12. A method for producing a charge-transporting thin film, comprising the steps of applying the charge-transporting varnish of 7 or 8 above to a substrate and evaporating off the solvent.

13. A method for producing the fluorine atom-containing polymer of 1 above, comprising the step of condensation polymerizing a fluorene derivative of formula (1') below, a fluorene derivative of formula (2') below and a fluorene derivative of formula (3') below

[Chemical Formula 2]

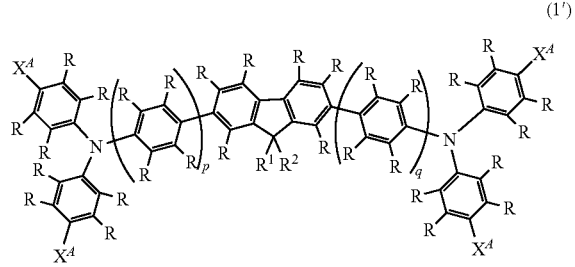

(1')

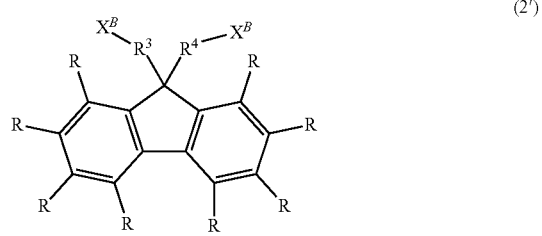

(2')

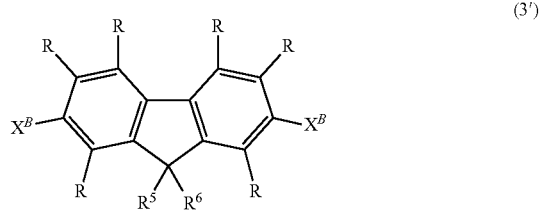

(3')

wherein $R^1$ to $R^6$, R, p and q are as defined above; each $X^A$ is independently a halogen atom or a pseudo-halogen group; and each $X^B$ is independently a group of formula (4) or (5) below

[Chemical Formula 3]

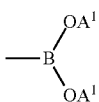
(4)

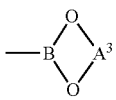
(5)

wherein $A^1$ and $A^2$ are each independently a hydrogen atom, an alkyl group of 1 to 20 carbon atoms or an aryl group of 6 to 20 carbon atoms; and $A^3$ is an alkanediyl group of 1 to 20 carbon atoms or an arylene group of 6 to 20 carbon atoms.

14. A fluorene derivative of the following formula

[Chemical Formula 4]

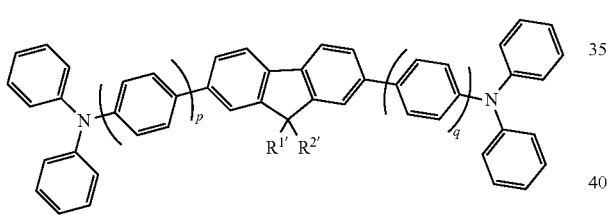

wherein $R^{1'}$ and $R^{2'}$ are alkyl groups of 2 to 20 carbon atoms which include at least one ether structure; and p and q are each independently 0 or 1.

15. A fluorene derivative of the following formula

[Chemical Formula 5]

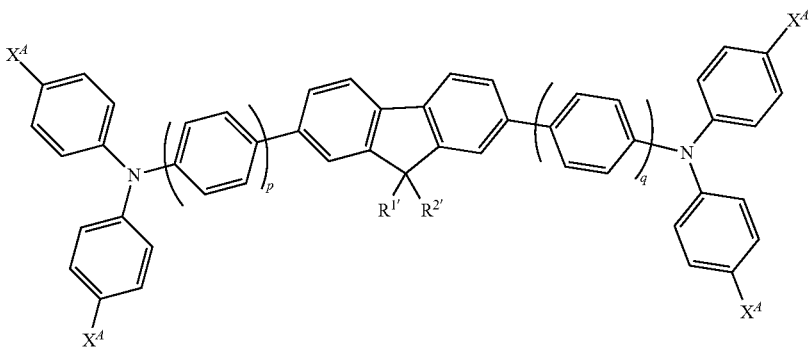

wherein $R^{1'}$ and $R^{2'}$ are alkyl groups of 2 to 20 carbon atoms which include at least one ether structure;

each $X^A$ is independently a halogen atom or a pseudohalogen group; and p and q are each independently 0 or 1.

16. A fluorene derivative of the following formula

[Chemical Formula 6]

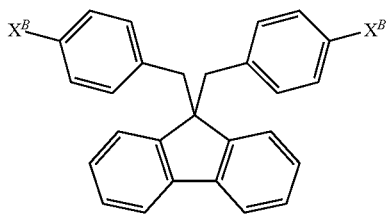

wherein each $X^B$ is independently a group of formula (4) or (5) below

[Chemical Formula 7]

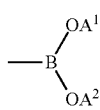
(4)

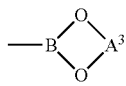
(5)

wherein $A^1$ and $A^2$ are each independently a hydrogen atom, an alkyl group of 1 to 20 carbon atoms or an aryl group of 6 to 20 carbon atoms; and $A^3$ is an alkanediyl group of 1 to 20 carbon atoms or an arylene group of 6 to 20 carbon atoms.

17. A fluorene derivative of the following formula

[Chemical Formula 8]

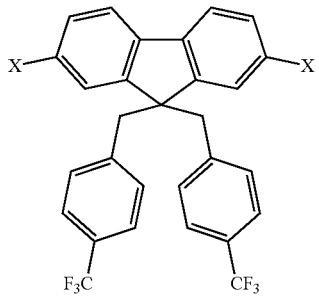

wherein each X is independently a halogen atom, a pseudo-halogen group, or a group of formula (4) or (5) below

[Chemical Formula 9]

wherein $A^1$ and $A^2$ are each independently a hydrogen atom, an alkyl group of 1 to 20 carbon atoms or an aryl group of 6 to 20 carbon atoms; and $A^3$ is an alkanediyl group of 1 to 20 carbon atoms or an arylene group of 6 to 20 carbon atoms.

Advantageous Effects of the Invention

The fluorine atom-containing polymer of the invention can be suitably used as a charge-transporting substance and, even when the charge-transporting varnish of the invention containing this polymer is used to form a thin film as a single layer between an anode and a light-emitting layer in a form that contacts both, is able to achieve an organic EL device having excellent brightness characteristics. Although the reasons for this are not entirely clear, it is thought that, because the fluorine atom-containing charge-transporting substance readily migrates to the face side (light-emitting layer side) of the thin film, there arises an uneven distribution of the fluorine atom-containing charge-transporting substance primarily on the face side (light-emitting layer side) of the thin film and of the charge-transporting substrate that contains no fluorine atoms primarily on the back side (anode side) of the thin film, leading to phase separation within the single layer into a hole-injecting region and a hole-transporting region, with hole-injecting constituents decreasing and hole-transporting constituents increasing from the anode electrode toward the light-emitting layer. As a result, the thin-film functions as a hole-injecting-and-transporting layer similar to cases in which these two layers are present.

By using the charge-transporting varnish of the invention, the functional multilayer film in a device can be replaced by a single-layer film, enabling higher yield and lower costs due to simplification of the manufacturing process conditions, and also making it possible to achieve devices that are, for example, more lightweight and compact. Also, the charge-transporting varnish of the invention can reproducibly produce thin films of excellent charge transportability even using various wet processes capable of film formation over a large surface area, such as spin coating or slit coating, and is thus capable of fully accommodating recent advances in the field of organic EL devices.

In addition, thin films obtained from the charge-transporting varnish of the invention can also be used as, for example, antistatic coatings or as anode buffer layers in organic thin-film solar cells.

EMBODIMENT FOR CARRYING OUT THE INVENTION

Figure 1A:
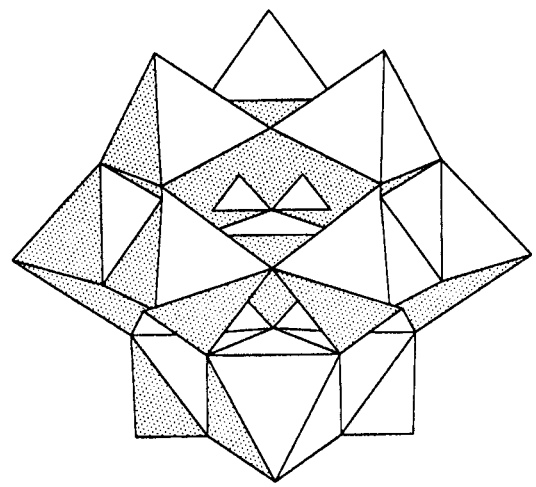
FIG. 1A shows a Keggin-type chemical structure.

[Fluorine Atom-Containing Polymer]
The fluorine atom-containing polymer of the invention is a condensation polymer of a fluorene derivative that provides recurring units of formula (1) below, a fluorene derivative that provides recurring units of formula (2) below and a fluorene derivative that provides recurring units of formula (3) below.

[Chemcial Formula 10]

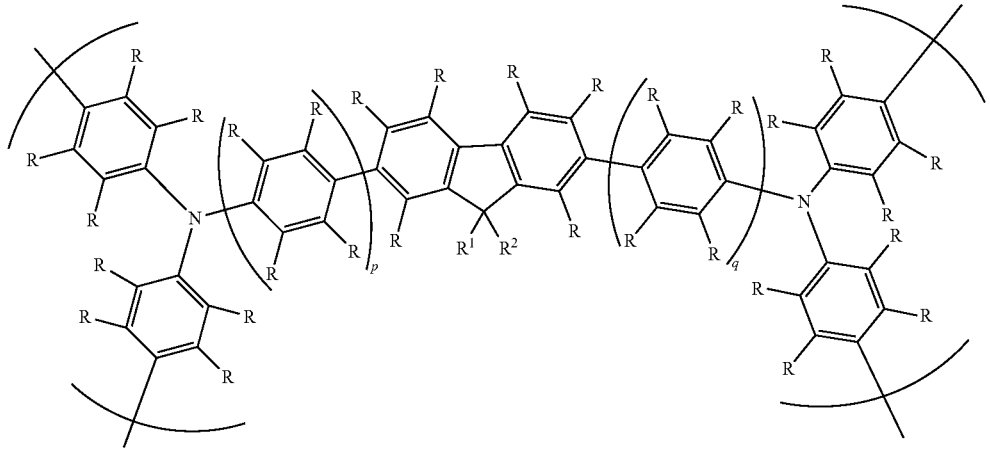

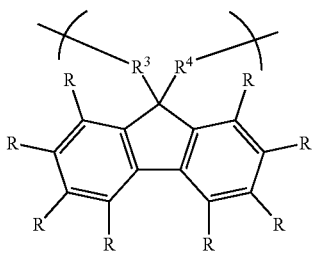 (2)

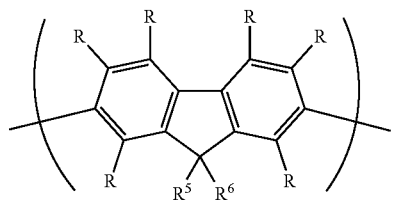 (3)

In formula (1), $R^1$ and $R^2$ are each independently a hydrogen atom, an alkyl group of 1 to 20 carbon atoms, an alkenyl group of 2 to 20 carbon atoms, an alkynyl group of 2 to 20 carbon atoms, an aryl group of 6 to 20 carbon atoms, a heteroaryl group of 2 to 20 carbon atoms, an alkoxy group of 1 to 20 carbon atoms, an alkenyloxy group of 2 to 20 carbon atoms, an alkynyloxy group of 2 to 20 carbon atoms, an aryloxy group of 6 to 20 carbon atoms, a heteroaryloxy group of 2 to 20 carbon atoms or an alkyl group of 2 to 20 carbon atoms which includes at least one ether structure, with the proviso that at least one of $R^1$ and $R^2$ is such an alkyl group, alkoxy group, alkenyloxy group, alkynyloxy group, aryloxy group, heteroaryloxy group, or alkyl group which includes at least one ether structure.

The alkyl group of 1 to 20 carbon atoms may be linear, branched or cyclic. Examples include linear or branched alkyl groups of 1 to 20 carbon atoms, such as methyl, ethyl, n-propyl, isopropyl, n-butyl, isobutyl, s-butyl, t-butyl, n-pentyl, n-hexyl, n-heptyl, n-octyl, n-nonyl and n-decyl groups; and cyclic alkyl groups of 3 to 20 carbon atoms, such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

The alkenyl group of 2 to 20 carbon atoms may be linear, branched or cyclic. Examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl and n-1-eicosenyl groups.

The alkynyl group of 2 to 20 carbon atoms may be linear, branched or cyclic. Examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

Examples of aryl groups of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Examples of heteroaryl groups of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

The alkoxy group of 1 to 20 carbon atoms may be linear, branched or cyclic. Examples include linear or branched alkoxy groups of 1 to 20 carbon atoms, such as methoxy, ethoxy, n-propoxy, isopropoxy, n-butoxy, isobutoxy, s-butoxy, t-butoxy, n-pentyloxy, n-hexyloxy, n-heptyloxy, n-octyloxy, n-nonyloxy and n-decyloxy groups; and cyclic alkoxy groups of 3 to 20 carbon atoms, such as cyclopropyloxy, cyclobutyloxy, cyclopentyloxy, cyclohexyloxy, cycloheptyloxy, cyclooctyloxy, cyclononyloxy, cyclodecyloxy, bicyclobutyloxy, bicyclopentyloxy, bicyclohexyloxy, bicycloheptyloxy, bicyclooctyloxy, bicyclononyloxy and bicyclodecyloxy groups.

The alkenyloxy group of 2 to 20 carbon atoms may be linear, branched or cyclic. Examples include ethenyloxy, n-1-propenyloxy, n-2-propenyloxy, 1-methylethenyloxy, n-1-butenyloxy, n-2-butenyloxy, n-3-butenyloxy, 2-methyl-1-propenyloxy, 2-methyl-2-propenyloxy, 1-ethylethenyloxy, 1-methyl-1-propenyloxy, 1-methyl-2-propenyloxy, n-1-pentenyloxy, n-1-decenyloxy and n-1-eicosenyloxy groups.

The alkynyloxy group of 2 to 20 carbon atoms may be linear, branched or cyclic. Examples include ethynyloxy, n-1-propynyloxy, n-2-propynyloxy, n-1-butynyloxy, n-2-butynyloxy, n-3-butynyloxy, 1-methyl-2-propynyloxy, n-1-pentynyloxy, n-2-pentynyloxy, n-3-pentynyloxy, n-4-pentynyloxy, 1-methyl-n-butynyloxy, 2-methyl-n-butynyloxy, 3-methyl-n-butynyloxy, 1,1-dimethyl-n-propynyloxy, n-1-hexynyloxy, n-1-decynyloxy, n-1-pentadecynyloxy and n-1-eicosynyloxy groups.

Examples of aryloxy groups of 6 to 20 carbon atoms include phenyloxy, 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy and 9-phenanthryloxy groups.

Examples of heteroaryloxy groups of 2 to 20 carbon atoms include 2-thienyloxy, 3-thienyloxy, 2-furanyloxy, 3-furanyloxy, 2-oxazolyloxy, 4-oxazolyloxy, 5-oxazolyloxy, 3-isooxazolyloxy, 4-isooxazolyloxy, 5-isooxazolyloxy, 2-thiazolyloxy, 4-thiazolyloxy, 5-thiazolyloxy, 3-isothiazolyloxy, 4-isothiazolyloxy, 5-isothiazolyloxy, 2-imidazolyloxy, 4-imidazolyloxy, 2-pyridyloxy, 3-pyridyloxy and 4-pyridyloxy groups.

The alkyl group of 2 to 20 carbon atoms which includes at least one ether structure is exemplified by linear or branched alkyl groups in which at least one methylene group is substituted with an oxygen atom. However, it is not one in which a methylene group bonded to a fluorene structure is substituted with an oxygen atom; nor is it one in which neighboring methylene groups are at the same time substituted with oxygen atoms. Taking into account the availability of the starting compounds, such a group is preferably a group of formula (A), and more preferably a group of formula (B).

—(R$^A$O)$_r$—R$^B$ (A)

—(CH$_2$CH$_2$O)$_r$—CH$_3$ (B)

In these formulas, $R^A$ is a linear or branched alkylene group of 1 to 4 carbon atoms, $R^B$ is a linear or branched alkyl group of from 1 to [20−(number of carbon atoms in $R^A$)×r]carbon atoms, and the subscript r is an integer from 1 to 9. From the standpoint of compatibility with the dopant, r is preferably at least 2, and more preferably at least 3; from the standpoint of the availability of the starting compounds, r is preferably 5 or less, and more preferably 4 or less.

Examples of alkyl groups of 2 to 20 carbon atoms which include at least one ether structure include —CH$_2$OCH$_3$, —CH$_2$OCH$_2$CH$_3$, —CH$_2$O(CH$_2$)$_2$CH$_3$, —CH$_2$OCH(CH$_3$)$_2$, —CH$_2$O(CH$_2$)$_3$CH$_3$, —CH$_2$OCH$_2$CH(CH$_3$)$_2$, —CH$_2$OC(CH$_3$)$_3$, —CH$_2$O(CH$_2$)$_4$CH$_3$, —CH$_2$OCH(CH$_3$)(CH$_2$)$_2$CH$_3$, —CH$_2$O(CH$_2$)$_2$CH(CH$_3$)$_2$, —CH$_2$OCH(CH$_3$)(CH$_2$)$_3$CH$_3$, —CH$_2$O(CH$_2$)$_5$CH$_3$, —CH$_2$OCH$_2$CH(CH$_3$)(CH$_2$)$_2$CH$_3$, —CH$_2$O(CH$_2$)$_2$CH(CH$_3$)CH$_2$CH$_3$, —CH$_2$O(CH$_2$)$_3$CH(CH$_3$)$_2$, —CH$_2$OC(CH$_3$)$_2$(CH$_2$)$_2$CH$_3$, —CH$_2$OCH(CH$_2$CH$_3$)(CH$_2$)$_2$CH$_3$, —CH$_2$OC(CH$_3$)$_2$CH(CH$_3$)$_2$, —CH$_2$O(CH$_2$)$_6$CH$_3$, —CH$_2$O(CH$_2$)$_7$CH$_3$, —CH$_2$OCH$_2$CH(CH$_2$CH$_3$)(CH$_2$)$_3$CH$_3$, —CH$_2$O(CH$_2$)$_8$CH$_3$, —CH$_2$O(CH$_2$)$_9$CH$_3$, —CH$_2$O(CH$_2$)$_{10}$CH$_3$, —CH$_2$O(CH$_2$)$_{11}$CH$_3$, —CH$_2$O(CH$_2$)$_{12}$CH$_3$, —CH$_2$O(CH$_2$)$_{13}$CH$_3$, —CH$_2$O(CH$_2$)$_{14}$CH$_3$, —CH$_2$O(CH$_2$)$_{15}$CH$_3$, —CH$_2$O(CH$_2$)$_{16}$CH$_3$, —CH$_2$O(CH$_2$)$_{17}$CH$_3$, —CH$_2$O(CH$_2$)$_{18}$CH$_3$, —CH$_2$CH$_2$OCH$_3$, —CH$_2$CH$_2$OCH$_2$CH$_3$, —CH$_2$CH$_2$O(CH$_2$)$_2$CH$_3$, —CH$_2$CH$_2$OCH(CH$_3$)$_2$, —CH$_2$CH$_2$O(CH$_2$)$_3$CH$_3$, —CH$_2$CH$_2$OCH$_2$CH(CH$_3$)$_2$, —CH$_2$CH$_2$OC(CH$_3$)$_3$, —CH$_2$CH$_2$O(CH$_2$)$_4$CH$_3$, —CH$_2$CH$_2$OCH(CH$_3$)(CH$_2$)$_2$CH$_3$, —CH$_2$CH$_2$OCH(CH$_3$)$_2$, —CH$_2$CH$_2$O(CH$_2$)$_2$CH(CH$_3$)$_2$, —CH$_2$CH$_2$OC(CH$_3$)$_3$, —CH$_2$CH$_2$OCH(CH$_3$)(CH$_2$)$_3$CH$_3$, —CH$_2$CH$_2$O(CH$_2$)$_5$CH$_3$, —CH$_2$CH$_2$OCH(CH$_3$)(CH$_2$)$_3$CH$_3$, —CH$_2$CH$_2$OCH$_2$CH(CH$_3$)(CH$_2$)$_2$CH$_3$, —CH$_2$CH$_2$O(CH$_2$)$_2$CH(CH$_3$)CH$_2$CH$_3$, —CH$_2$CH$_2$O(CH$_2$)$_3$CH(CH$_3$)$_2$, —CH$_2$CH$_2$OC(CH$_3$)$_2$(CH$_2$)$_2$CH$_3$, —CH$_2$CH$_2$OCH(CH$_2$CH$_3$)(CH$_2$)$_2$CH$_3$, —CH$_2$CH$_2$OC(CH$_3$)$_2$CH(CH$_3$)$_2$, —CH$_2$CH$_2$O(CH$_2$)$_6$CH$_3$, —CH$_2$CH$_2$O(CH$_2$)$_7$CH$_3$, —CH$_2$CH$_2$OCH$_2$CH(CH$_2$CH$_3$)(CH$_2$)$_3$CH$_3$, —CH$_2$CH$_2$O(CH$_2$)$_8$CH$_3$, —CH$_2$CH$_2$O(CH$_2$)$_9$CH$_3$, —CH$_2$CH$_2$O(CH$_2$)$_{10}$CH$_3$, —CH$_2$CH$_2$O(CH$_2$)$_{11}$CH$_3$, —CH$_2$CH$_2$O(CH$_2$)$_{12}$CH$_3$, —CH$_2$CH$_2$O(CH$_2$)$_{13}$CH$_3$, —CH$_2$CH$_2$O(CH$_2$)$_{14}$CH$_3$, —CH$_2$CH$_2$O(CH$_2$)$_{15}$CH$_3$, —CH$_2$CH$_2$O(CH$_2$)$_{16}$CH$_3$, —CH$_2$CH$_2$CH$_2$OCH$_3$, —CH$_2$CH$_2$CH$_2$OCH$_2$CH$_3$, —CH$_2$CH$_2$CH$_2$O(CH$_2$)$_2$CH$_3$, —CH$_2$CH$_2$CH$_2$OCH(CH$_3$)$_2$, —CH$_2$CH$_2$CH$_2$O(CH$_2$)$_3$CH$_3$, —CH$_2$CH$_2$CH$_2$OCH$_2$CH(CH$_3$)$_2$, —CH$_2$CH$_2$CH$_2$OC(CH$_3$)$_3$, —CH$_2$CH$_2$CH$_2$O(CH$_2$)$_4$CH$_3$, —CH$_2$CH$_2$CH$_2$OCH(CH$_3$)(CH$_2$)$_2$CH$_3$, —CH$_2$CH$_2$CH$_2$OCH(CH$_3$)$_2$, —CH$_2$CH$_2$CH$_2$O(CH$_2$)$_2$CH(CH$_3$)$_2$, —CH$_2$CH$_2$CH$_2$OC(CH$_3$)$_3$, —CH$_2$CH$_2$CH$_2$OCH(CH$_3$)(CH$_2$)$_3$CH$_3$, —CH$_2$CH$_2$CH$_2$O(CH$_2$)$_5$CH$_3$, —CH$_2$CH$_2$CH$_2$OCH(CH$_3$)(CH$_2$)$_3$CH$_3$, —CH$_2$CH$_2$CH$_2$OCH$_2$CH(CH$_3$)(CH$_2$)$_2$CH$_3$, —CH$_2$CH$_2$CH$_2$O(CH$_2$)$_2$CH(CH$_3$)CH$_2$CH$_3$, —CH$_2$CH$_2$CH$_2$O(CH$_2$)$_3$CH(CH$_3$)$_2$, —CH$_2$CH$_2$CH$_2$OC(CH$_3$)$_2$(CH$_2$)$_2$CH$_3$, —CH$_2$CH$_2$CH$_2$OCH(CH$_2$CH$_3$)(CH$_2$)$_2$CH$_3$, —CH$_2$CH$_2$CH$_2$OC(CH$_3$)$_2$CH(CH$_3$)$_2$, —CH$_2$CH$_2$CH$_2$O(CH$_2$)$_6$CH$_3$, —CH$_2$CH$_2$CH$_2$O(CH$_2$)$_7$CH$_3$, —CH$_2$CH$_2$CH$_2$OCH$_2$CH(CH$_2$CH$_3$)(CH$_2$)$_3$CH$_3$, —CH$_2$CH$_2$OCH$_2$CH$_2$OCH$_3$, —CH$_2$CH$_2$OCH$_2$CH$_2$OCH$_2$CH$_2$OCH$_3$, —CH$_2$CH$_2$OCH$_2$CH$_2$OCH$_2$CH$_2$OCH$_2$CH$_2$OCH$_3$, —CH$_2$CH$_2$OCH$_2$CH$_2$OCH$_2$CH$_2$OCH$_2$CH$_2$OCH$_2$CH$_2$OCH$_3$, —CH$_2$CH$_2$OCH$_2$CH$_2$OCH$_2$CH$_2$OCH$_2$CH$_2$OCH$_2$CH$_2$OCH$_2$CH$_2$OCH$_3$, —CH$_2$CH$_2$OCH$_2$CH$_2$OCH$_2$CH$_2$OCH$_2$CH$_2$OCH$_2$CH$_2$OCH$_2$CH$_2$OCH$_2$CH$_2$OCH$_3$, —CH$_2$CH$_2$CH$_2$OCH$_2$CH$_2$CH$_2$OCH$_3$, —CH$_2$CH$_2$CH$_2$OCH$_2$CH$_2$CH$_2$OCH$_2$CH$_2$CH$_2$OCH$_3$, —CH$_2$CH$_2$CH$_2$OCH$_2$CH$_2$CH$_2$OCH$_2$CH$_2$CH$_2$OCH$_2$CH$_2$CH$_2$OCH$_3$, —CH$_2$CH$_2$CH$_2$CH$_2$OCH$_2$CH$_2$CH$_2$CH$_2$OCH$_3$, —CH$_2$CH$_2$CH$_2$CH$_2$OCH$_2$CH$_2$CH$_2$CH$_2$OCH$_2$CH$_2$CH$_2$CH$_2$OCH$_3$, —CH$_2$CH$_2$CH$_2$CH$_2$CH$_2$CH$_2$CH$_2$CH$_2$CH$_2$OCH$_2$CH$_2$CH$_2$CH$_2$OCH$_3$, —CH$_2$CH$_2$CH$_2$CH$_2$OCH$_2$CH$_2$CH$_2$OCH$_2$CH$_2$OCH$_3$ CH$_2$ CH$_2$CH$_2$OCH$_2$CH$_2$CH$_2$OCH$_3$, —CH$_2$CH$_2$OCH$_2$CH$_2$OCH$_2$CH$_2$OCH$_2$CH$_2$OCH$_2$CH$_2$OCH$_2$CH$_2$OCH$_2$CH$_2$OCH$_3$, —CH$_2$CH$_2$OCH$_2$CH$_2$OCH$_2$CH$_2$OCH$_2$CH$_2$OCH$_2$CH$_2$ OCH$_2$CH$_2$CH$_2$CH$_2$CH$_3$, —CH$_2$CH$_2$OCH$_2$CH$_2$ CH$_2$CH$_2$CH$_2$CH$_2$CH$_2$OCH$_2$OCH$_2$CH$_2$CH$_2$OCH$_2$ CH$_3$, —CH$_2$CH$_2$OCH$_2$CH$_2$OCH$_2$CH$_3$, —CH$_2$CH$_2$OCH$_2$CH$_2$OCH$_2$CH$_2$OCH$_2$CH$_3$, —CH$_2$CH$_2$CH$_2$O(CH$_2$)$_8$CH$_3$, —CH$_2$CH$_2$CH$_2$O(CH$_2$)$_9$CH$_3$, —CH$_2$CH$_2$CH$_2$(CH$_2$)$_{10}$CH$_3$, —CH$_2$CH$_2$CH$_2$O(CH$_2$)$_{11}$CH$_3$, —CH$_2$CH$_2$CH$_2$O(CH$_2$)$_{12}$CH$_3$, —CH$_2$CH$_2$CH$_2$O(CH$_2$)$_{13}$CH$_3$, —CH$_2$CH$_2$CH$_2$O(CH$_2$)$_{14}$CH$_3$, —CH$_2$CH$_2$CH$_2$O(CH$_2$)$_{15}$CH$_3$ and —CH$_2$CH$_2$CH$_2$O(CH$_2$)$_{16}$CH$_3$.

In this invention, to balance the solubility of the fluorine atom-containing polymer in organic solvents with the compatibility of the polymer with the dopant when the polymer is rendered into a solid film (charge-transporting thin film), at least one of $R^1$ and $R^2$ is such an alkyl group, alkoxy group, alkenyloxy group, alkynyloxy group, aryloxy group, heteroaryloxy group, or alkyl group which includes at least one ether structure; preferably, both $R^1$ and $R^2$ are any of these groups. Also, taking into account the availability of the starting compounds and properties such as the charge transportability of the resulting polymer and the resulting thin film, it is preferable for at least one of $R^1$ and $R^2$ to be an alkyl group or an alkyl group of 2 to 20 carbon atoms which includes at least one ether structure, and even more preferable for both $R^1$ and $R^2$ to be an alkyl group or an alkyl group of 2 to 20 carbon atoms which includes at least one ether structure. Taking into account the affinity of the compound with the solvent, it is even more preferable for both $R^1$ and $R^2$ to be alkyl groups of 2 to 20 carbon atoms which include at least one ether structure.

In formula (1), p and q are each independently 0 or 1. From the standpoint of the ease of synthesizing the compound, p and q are preferably both 0 or both 1.

In formula (2), $R^3$ and $R^4$ are each independently a nonconjugated divalent organic group. The nonconjugated divalent organic group is not particularly limited, although from the standpoint of polymerizability, —R$^c$—Ar— (wherein Re is an alkylene group of 1 to 20 carbon atoms, and Ar is an arylene group of 6 to 20 carbon atoms) is preferred.

Examples of nonconjugated divalent organic groups include, but are not limited to, the groups shown below.

[Chemical Formula 11]

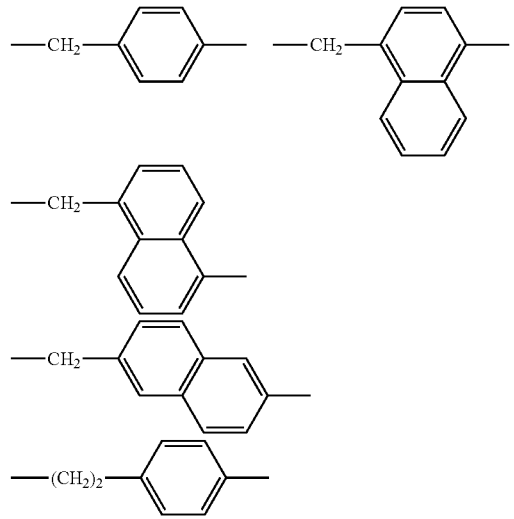

-continued

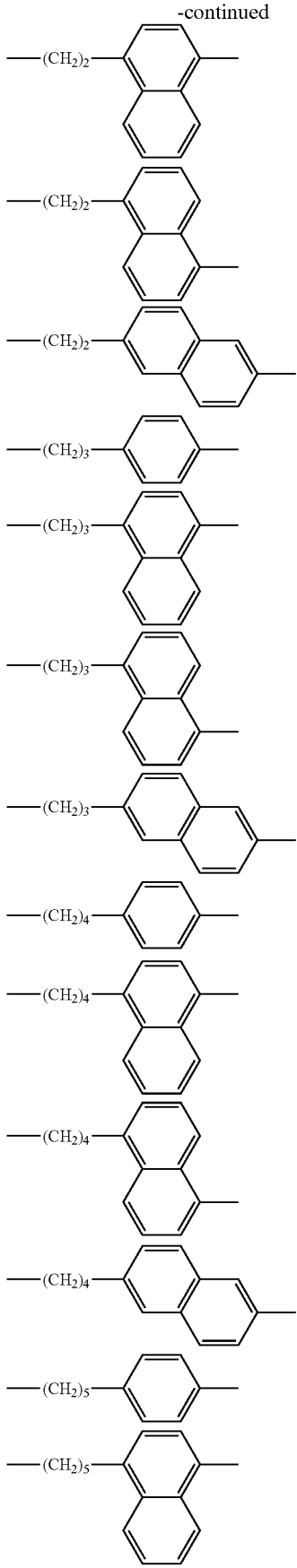

-continued

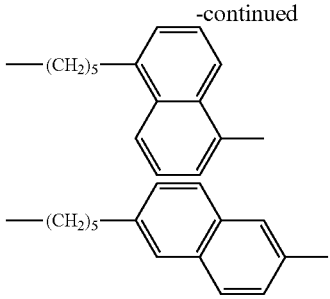

In formula (3), $R^5$ is a hydrogen atom, or an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom may be substituted with a fluorine atom.

$R^5$ is preferably an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom is substituted with a fluorine atom.

In formula (3), $R^6$ is an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom is substituted with a fluorine atom.

Examples of aralkyl groups of 7 to 20 carbon atoms include benzyl, phenylethyl, phenylpropyl, naphthylmethyl, naphthylethyl and naphthylpropyl groups.

Examples of alkylaralkyl groups of 8 to 20 carbon atoms include methylbenzyl, ethylbenzyl, n-propylbenzyl, isopropylbenzyl, n-butylbenzyl, isobutylbenzyl, s-butylbenzyl, t-butylbenzyl, n-pentylbenzyl, n-hexylbenzyl, n-heptylbenzyl, n-octylbenzyl, n-nonylbenzyl, n-decylbenzyl, methylphenylethyl, ethylphenylethyl, n-propylphenylethyl, isopropylphenylethyl, n-butylphenylethyl, isobutylphenylethyl, s-butylphenylethyl, t-butylphenylethyl, n-pentylphenylethyl, n-hexylphenylethyl, n-heptylphenylethyl, n-octylphenylethyl, n-nonylphenylethyl, n-decylphenylethyl, methylphenylpropyl, ethylphenylpropyl, n-propylphenylpropyl, isopropylphenylpropyl, n-butylphenylpropyl, isobutylphenylpropyl, s-butylphenylpropyl, t-butylphenylpropyl, n-pentylphenylpropyl, n-hexylphenylpropyl, n-heptylphenylpropyl, n-octylphenylpropyl, n-nonylphenylpropyl, n-decylphenylpropyl, methylnaphthylmethyl, ethylnaphthylmethyl, n-propylnaphthylmethyl, isopropylnaphthylmethyl, n-butylnaphthylmethyl, isobutylnaphthylmethyl, s-butylnaphthylmethyl, t-butylnaphthylmethyl, n-pentylnaphthylmethyl, n-hexylnaphthylmethyl, n-heptylnaphthylmethyl, n-octylnaphthylmethyl, n-nonylnaphthylmethyl, n-decylnaphthylmethyl, methylnaphthylethyl, ethylnaphthylethyl, n-propylnaphthylethyl, isopropylnaphthylethyl, n-butylnaphthylethyl, isobutylnaphthylethyl, s-butylnaphthylethyl, t-butylnaphthylethyl, n-pentylnaphthylethyl, n-hexylnaphthylethyl, n-heptylnaphthylethyl, n-octylnaphthylethyl, n-nonylnaphthylethyl, n-decylnaphthylethyl, methylnaphthylpropyl, ethylnaphthylpropyl, n-propylnaphthylpropyl, isopropylnaphthylpropyl, n-butylnaphthylpropyl, isobutylnaphthylpropyl, s-butylnaphthylpropyl, t-butylnaphthylpropyl, n-pentylnaphthylpropyl, n-hexylnaphthylpropyl, n-heptylnaphthylpropyl, n-octylnaphthylpropyl, n-nonylnaphthylpropyl and n-decylnaphthylpropyl groups.

The alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, heteroaryl group of 2 to 20 carbon atoms, aryloxy group of 6 to 20 carbon atoms and heteroaryloxy group of 2 to 20 carbon atoms are each exemplified in the same way as above.

Of these, $R^5$ and $R^6$ are each preferably an alkyl group of 1 to 20 carbon atoms, alkoxy group of 1 to 20 carbon atoms or alkylaralkyl group of 8 to 20 carbon atoms in which at least one hydrogen atom is substituted with a fluorine atom. In particular, because placing a fluorine atom-containing group outside of the conjugated system imparts no influence on the electronic state of the polymer, an alkylaralkyl group of 8 to 20 carbon atoms in which at least one hydrogen atom on the alkyl moiety is substituted with a fluorine atom is preferred.

Preferred examples include trifluoromethyl, 2,2,2-trifluoroethyl, pentafluoroethyl, 2,2,3,3-tetrafluoropropyl, 2,2,3,3,3-pentafluoropropyl, heptafluoropropyl, 2,2,2-trifluoro-1-(trifluoromethyl)ethyl, nonafluorobutyl, 4,4,4-trifluorobutyl, undecafluoropentyl, 2,2,3,3,4,4,5,5,5-nonafluoropentyl, 2,2,3,3,4,4,5,5-octafluoropentyl, tridecafluorohexyl, 2,2,3,3,4,4,5,5,6,6,6-undecafluorohexyl, 2,2,3,3,4,4,5,5,6,6-decafluorohexyl, 3,3,4,4,5,5,6,6,6-nonafluorohexyl, trifluoromethoxy, 2,2,2-trifluoroethoxy, pentafluoroethoxy, 2,2,3,3-tetrafluoropropoxy, 2,2,3,3-pentafluoropropoxy, heptafluoropropoxy, 2,2,2-trifluoro-1-(trifluoromethyl)ethoxy, 4,4,4-trifluorobutoxy, nonafluorobutoxy, 2,2,3,3,4,4,5,5-octafluoropentyloxy, 2,2,3,3,4,4,5,5,5-nonafluoropentyloxy, undecafluoropentyloxy, 3,3,4,4,5,5,6,6,6-nonafluorohexyloxy, 2,2,3,3,4,4,5,5,6,6-decafluorohexyloxy, 2,2,3,3,4,4,5,5,6,6-undecafluorohexyloxy, tridecafluorohexyloxy, trifluoromethylbenzyl, 2,2,2-trifluoroethylbenzyl, pentafluoroethylbenzyl, 2,2,3,3-tetrafluoropropylbenzyl, 2,2,3,3,3-pentafluoropropylbenzyl, heptafluoropropylbenzyl, trifluoromethylphenylethyl, 2,2,2-trifluoroethylphenylethyl, pentafluoroethylphenylethyl, 2,2,3,3-tetrafluoropropylphenylethyl, 2,2,3,3,3-pentafluoropropylphenylethyl, heptafluoropropylphenylethyl, trifluoromethylnaphthylmethyl, 2,2,2-trifluoroethylnaphthylmethyl, pentafluoroethylnaphthylmethyl, 2,2,3,3-tetrafluoropropylnaphthylmethyl, 2,2,3,3,3-pentafluoropropylnaphthylmethyl, heptafluoropropylnaphthylmethyl, trifluoromethylnaphthylethyl, 2,2,2-trifluoroethylnaphthylethyl, pentafluoroethylnaphthylethyl, 2,2,3,3-tetrafluoropropylnaphthylethyl, 2,2,3,3,3-pentafluoropropylnaphthylethyl and heptafluoropropylnaphthylether groups.

In formulas (1) to (3), each R is independently a halogen atom, a nitro group, a cyano group, an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms or alkynyloxy group of 2 to 20 carbon atoms which may be substituted with $Z^1$, or an aryl group of 6 to 20 carbon atoms, heteroaryl group of 2 to 20 carbon atoms, aryloxy group of 6 to 20 carbon atoms or heteroaryloxy group of 2 to 20 carbon atoms which may be substituted with $Z^2$.

$Z^1$ is a halogen atom, a nitro group, a cyano group, or an aryl group of 6 to 20 carbon atoms, heteroaryl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms or heteroaryl group of 2 to 20 carbon atoms which may be substituted with $Z^3$.

$Z^2$ is a halogen atom, a nitro group, a cyano group, or an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms or heteroaryl group of 2 to 20 carbon atoms which may be substituted with $Z^3$.

$Z^3$ is a halogen atom, a nitro group or a cyano group.

Examples of halogen atoms include fluorine, chlorine, bromine and iodine atoms.

R is preferably a hydrogen atom, a halogen atom, a nitro group, a cyano group or an alkyl group of 1 to 20 carbon atoms which may be substituted with $Z^1$; more preferably a hydrogen atom, a fluorine atom or an alkyl group of 1 to 4 carbon atoms which may be substituted with $Z^1$; and most preferably a hydrogen atom.

In this invention, the ratio between recurring units of formula (1) in the polymer and recurring units of formula (2) and recurring units of formula (3) combined is such that, expressed as a molar ratio, the amount of recurring units of formula (2) and recurring units of formula (3) combined with respect to unity (1) for recurring units of formula (1) is from about 1 to about 4. Also, from the standpoint of solubility and hole transportability, the ratio between recurring units of formula (2) and recurring units of formula (3) in the polymer is such that the amount of recurring units of formula (3) with respect to unity (1) for recurring units of formula (2) is preferably from about 0.7 to about 1.3, more preferably from about 0.8 to about 1.2, and even more preferably from about 0.9 to about 1.1.

The weight-average molecular weight (Mw) of the fluorine atom-containing polymer of the invention has a lower limit which, from the standpoint of increasing the charge transportability of the polymer, is preferably 1,000, more preferably 5,000, and even more preferably 10,000. The upper limit, from the standpoint of increasing the solubility of the polymer, is preferably 200,000, more preferably 150,000, and even more preferably 100,000. In this invention, Mw and the number-average molecular weight (Mn) are polystyrene-equivalent weight-average molecular weights obtained by gel permeation chromatography (GPC).

[Method of Synthesizing Fluorine Atom-Containing Polymer]

The fluorine atom-containing polymer of the invention can be synthesized by condensation polymerization of a fluorene derivative that provides recurring units of formula (1), a fluorene derivative that provides recurring units of formula (2) and a fluorene derivative that provides recurring units of formula (3).

For example, as shown in Scheme A below, the polymer can be synthesized by a coupling reaction between a fluorene derivative of formula (1'), a fluorene derivative of formula (2') and a fluorene derivative of formula (3'). This is explained below using, by way of illustration, a case involving synthesis by the Suzuki-Miyaura coupling reaction.

Scheme A
[Chemical Formula 12]
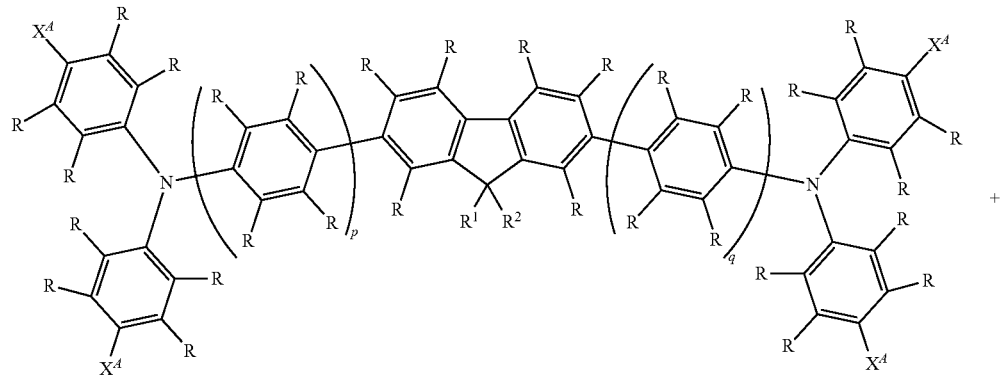
(1')
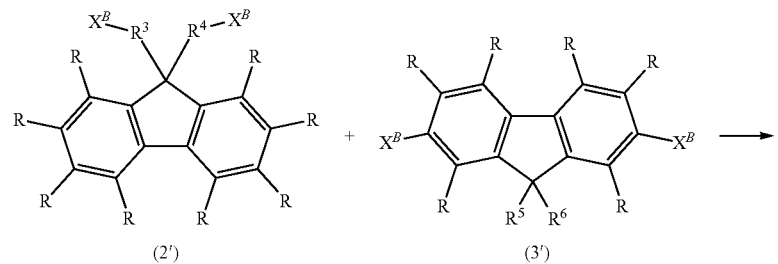
(2')  (3')
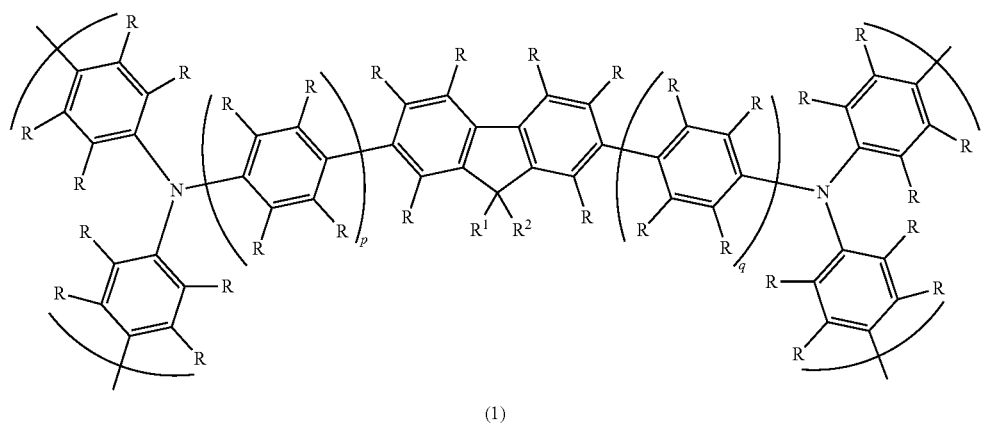
(1)
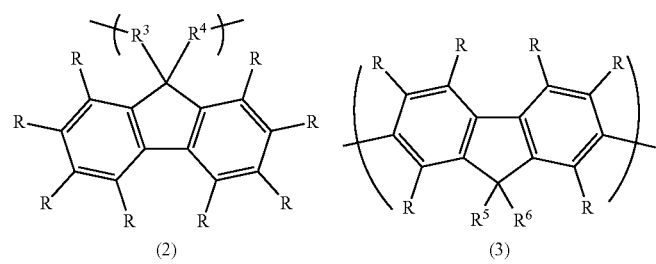
(2)  (3)

Here, $R^1$ to $R^6$, R, p and q are as defined above. Each $X^A$ is independently a halogen atom or a pseudo-halogen group. Each $X^B$ is independently a group of formula (4) or (5) below.

[Chemical Formula 13]

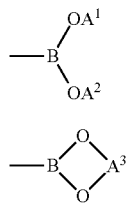

(4)

(5)

In formulas (4) and (5), $A^1$ and $A^2$ are each independently a hydrogen atom, an alkyl group or 1 to 20 carbon atoms or an aryl group of 6 to 20 carbon atoms. $A^3$ is an alkanediyl group of 1 to 20 carbon atoms or an arylene group of 6 to 20 carbon atoms.

The halogen atom, alkyl group and aryl group are exemplified in the same way as above.

Examples of pseudo-halogen groups include fluoroalkylsulfonyloxy groups such as methanesulfonyloxy, trifluoromethanesulfonyloxy and nonafluorobutanesulfonyloxy groups; and aromatic sulfonyloxy groups such as benzenesulfonyloxy and toluenesulfonyloxy groups.

Examples of alkanediyl groups of 1 to 20 carbon atoms include methylene, ethylene, propane-1,2-diyl, propane-1,3-diyl, 2,2-dimethylpropane-1,3-diyl, 2-ethyl-2-methylpropane-1,3-diyl, 2,2-diethylpropane-1,3-diyl, 2-methyl-2-propylpropane-1,3-diyl, butane-1,3-diyl, butane-2,3-diyl, butane-1,4-diyl, 2-methylbutane-2,3-diyl, 2,3-dimethylbutane-2,3-diyl, pentane-1,3-diyl, pentane-1,5-diyl, pentane-2,3-diyl, pentane-2,4-diyl, 2-methylpentane-2,3-diyl, 3-methylpentane-2,3-diyl, 4-methylpentane-2,3-diyl, 2,3-dimethylpentane-2,3-diyl, 3-methylpentane-2,4-diyl, 3-ethylpentane-2,4-diyl, 3,3-dimethylpentane-2,4-diyl, 3,3-dimethylpentane-2,4-diyl, 2,4-dimethylpentane-2,4-diyl, hexane-1,6-diyl, hexane-1,2-diyl, hexane-1,3-diyl, hexane-2,3-diyl, hexane-2,4-diyl, hexane-2,5-diyl, 2-methylhexane-2,3-diyl, 4-methylhexane-2,3-diyl, 3-methylhexane-2,4-diyl, 2,3-dimethylhexane-2,4-diyl, 2,4-dimethylhexane-2,4-diyl, 2,5-dimethylhexane-2,4-diyl, 2-methylhexane-2,5-diyl, 3-methylhexane-2,5-diyl and 2,5-dimethylhexane-2,5-diyl groups.

Examples of the arylene group of 6 to 20 carbon atoms include 1,2-phenylene, 1,2-naphthalene, 2,3-naphthylene, 1,8-naphthylene, 1,2-anthrylene, 2,3-anthrylene, 1,2-phenanthrylene, 3,4-phenanthrylene and 9,10-phenanthrylene groups.

The condensation reaction may be carried out in the absence of a solvent, although it is generally carried out using a solvent. Any solvent may be used so long as it is one that does not hinder the reaction. Illustrative examples include cyclic ethers such as tetrahydrofuran and 1,4-dioxane; amides such as N,N-dimethylformamide (DMF), N,N-dimethylacetamide (DMAc) and N-methyl-2-pyrrolidone (NMP); ketones such as methyl isobutyl ketone and cyclohexanone; halogenated hydrocarbons such as methylene chloride, chloroform, 1,2-dichloroethane and chlorobenzene; and aromatic hydrocarbons such as benzene, toluene and xylene. These solvents may be used singly or two or more may be used in admixture. Of these, 1,4-dioxane, toluene and xylene are especially preferred.

The catalyst used in the condensation reaction is exemplified by palladium catalysts such as [1,1'-bis(diphenylphosphino)ferrocene]palladium(II) dichloride ($PdCl_2$(dppf)), tetrakis(triphenylphosphine)palladium ($Pd(PPh_3)_4$), bis(triphenylphosphine)dichloropalladium ($Pd(PPh_3)_2Cl_2$), bis(benzylideneacetone)palladium ($Pd(dba)_2$), tris(benzylideneacetone)dipalladium ($Pd_2(dba)_3$), bis(tri-t-butylphosphine)palladium ($Pd(P-t-Bu_3)_2$) and palladium(II) acetate ($Pd(OAc)_2$).

The charging ratio between the fluorene derivative of formula (1') and the fluorene derivative of formula (2') and the fluorene derivative of formula (3') combined is such that, expressed as a molar ratio, the total number of moles of the fluorene derivative of formula (2') and the fluorene derivative of formula (3') per mole of the fluorene derivative of formula (1') is preferably from about 0.7 to about 1.3, and more preferably from about 0.8 to about 1.2.

The reaction temperature during condensation is generally from 40 to 200° C. The reaction time is variously selected according to the reaction temperature, but is generally from about 30 minutes to about 50 hours.

The fluorene derivative of formula (1') can be synthesized using a compound of formula (6) below as the starting material. First, as shown in Scheme B below, a compound of formula (6) is reacted with a compound of formula (7-1) and a compound of formula (7-2), thereby synthesizing an intermediate of formula (8). In the scheme shown below, $X^A$, $X^B$, $R^1$, $R^2$ and R are as defined above.

Scheme B

[Chemical Formula 14]

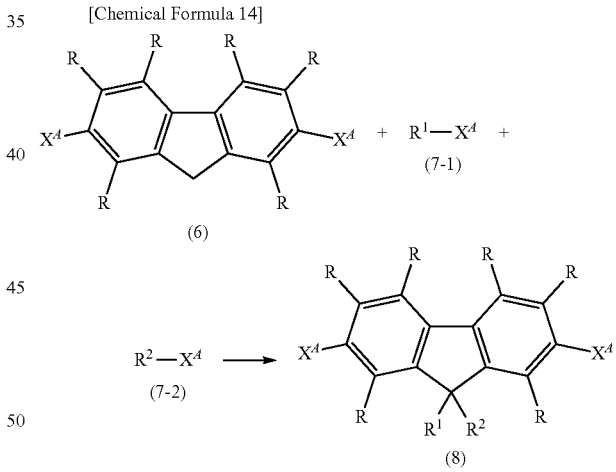

In the reaction shown in Scheme B, the charging ratios between the compound of formula (6) and, respectively, the compound of formula (7-1) and the compound of formula (7-2) are such that, expressed as molar ratios, the number of moles of the compound of formula (7-1) per mole of the compound formula (6) and the number of moles of the compound of formula (7-2) per mole of the compound of formula (6) are each from about 1 to about 3.

The solvent used in the reaction of Scheme B is exemplified by dimethylsulfoxide, N,N-dimethylformamide, N,N-dimethylacetamide, tetrahydrofuran, dioxane, acetonitrile and toluene. In terms of dissolving the starting compounds well and enabling the reaction to proceed smoothly, dimethylsulfoxide is preferred.

The reaction temperature may typically be from −50° C. to the boiling point of the solvent used, although the range of 0 to 100° C. is preferred. The reaction time is typically from 0.1 to 100 hours.

A fluorene derivative of formula (1') in which p and q are 0 can be synthesized by reacting the intermediate of formula (8) with a compound of formula (9) in the presence of a catalyst so as to synthesize an intermediate of formula (10) (Scheme C), and then halogenating this using a halogenating agent (Scheme D).

Scheme C

[Chemical Formula 15]

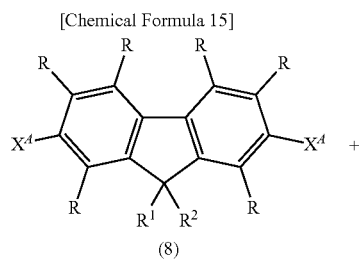

(8)

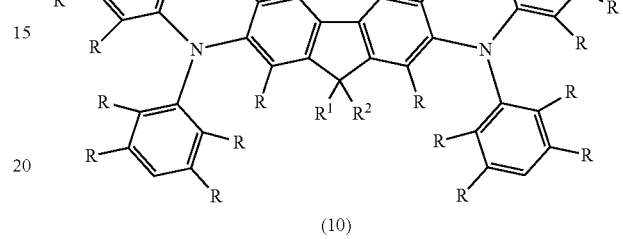

(9)

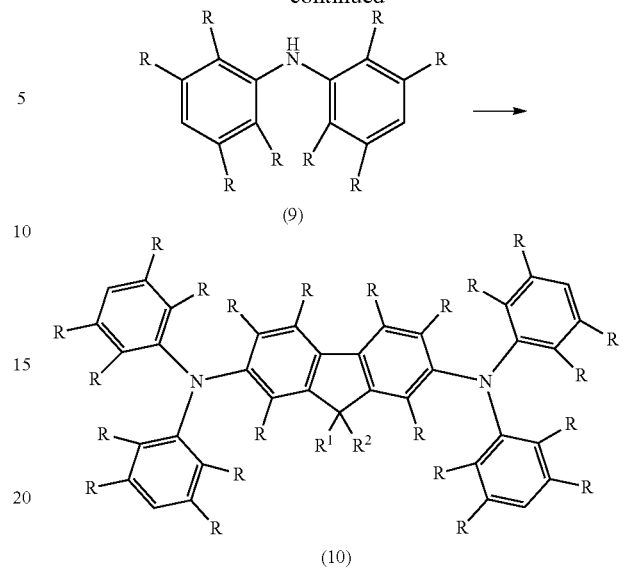

(10)

Scheme D

[Chemical Formula 16]

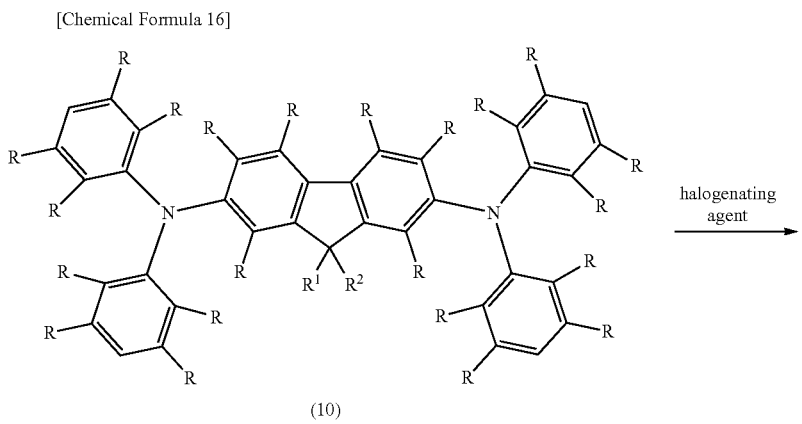

(10)

halogenating agent
→

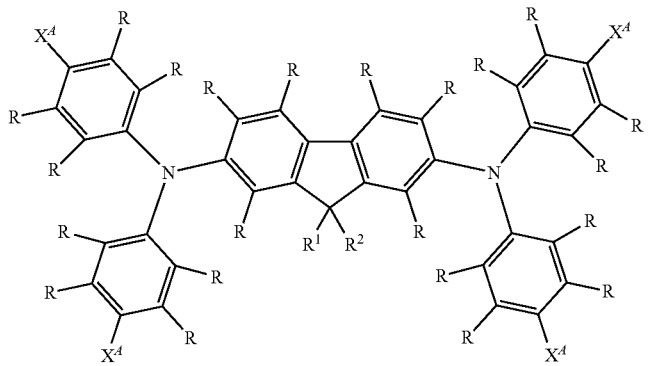

In the reaction shown in Scheme C, the charging ratio between the compound of formula (8) and the compound of formula (9), expressed as a molar ratio, is from about 2 to about 4 moles of the compound of formula (9) per mole of the compound of formula (8).

The catalyst used in the reaction shown in Scheme C is exemplified by the palladium catalysts mentioned above.

Examples of the solvent used in the reaction shown in Scheme C include toluene, dioxane, N,N-dimethylformamide and N,N-dimethylacetamide. From the standpoint of reactivity, preferred solvents include toluene and dioxane.

The reaction temperature may generally be from −50° C. to the boiling point of the solvent used, although the range of 0 to 140° C. is preferred. The reaction time is generally from 0.1 to 100 hours.

The reaction shown in Scheme D may use a known halogenating agent, one example of which is N-bromosuccinimide. This halogenating agent is used in an amount, expressed as a molar ratio, of about 4 to about 6 moles per mole of the compound of formula (10).

The solvent used in the reaction shown in Scheme D is exemplified by dimethylsulfoxide, N,N-dimethylformamide, N,N-dimethylacetamide, tetrahydrofuran, dioxane, acetonitrile, toluene and chloroform. In terms of dissolving well the starting compounds and enabling the reaction to proceed smoothly, dimethylsulfoxide, N,N-dimethylformamide and chloroform are preferred.

The reaction temperature may generally be from −50° C. to the boiling point of the solvent used, although the range of 0 to 140° C. is preferred. The reaction time is generally from 0.1 to 100 hours.

A fluorene derivative of formula (1') in which p and q are both 1 can be synthesized by reacting a compound of formula (11) with a compound of formula (12) in the presence of a catalyst so as to synthesize an intermediate of formula (13) (Scheme E), reacting the intermediate of formula (8) with the intermediate of formula (13) in the presence of a catalyst so as to synthesize an intermediate of formula (14) (Scheme F), and then halogenating this using a halogenating agent (Scheme G).

Scheme E

[Chemical Formula 17]

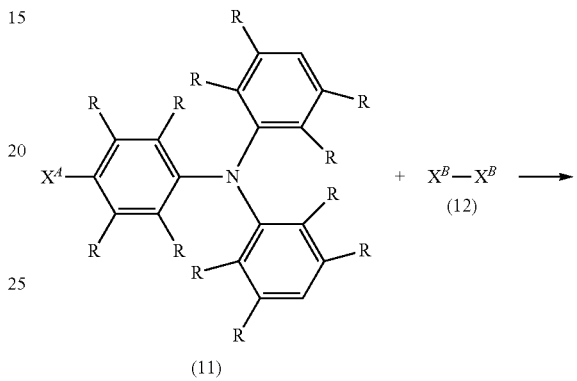

Scheme F

[Chemical Formula 18]

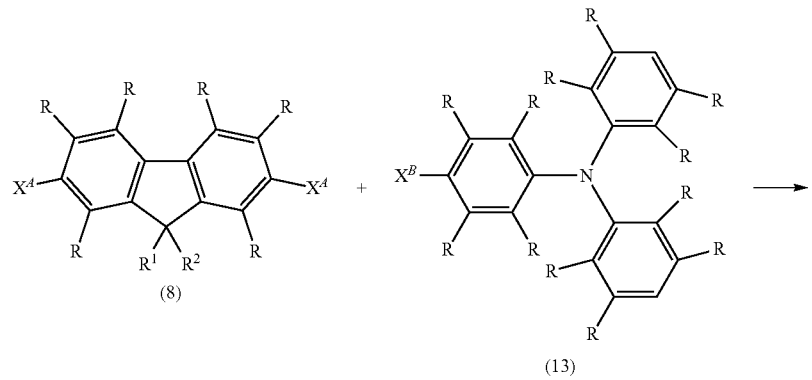

-continued

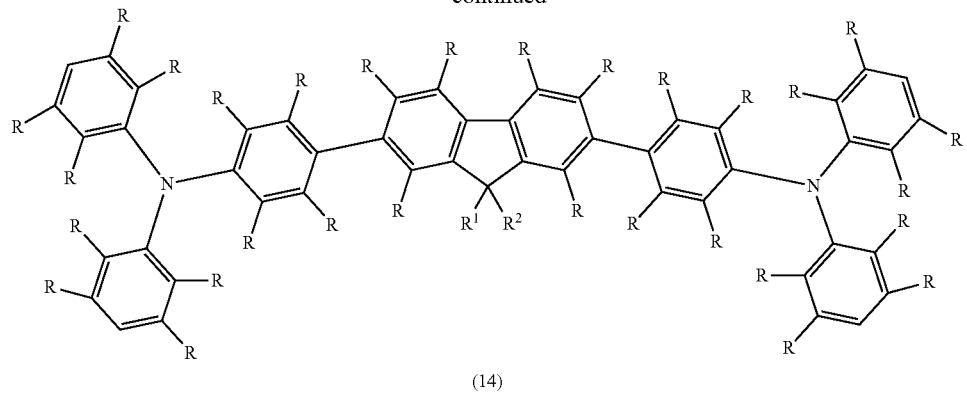

(14)

Scheme G

[Chemical Formula 19]

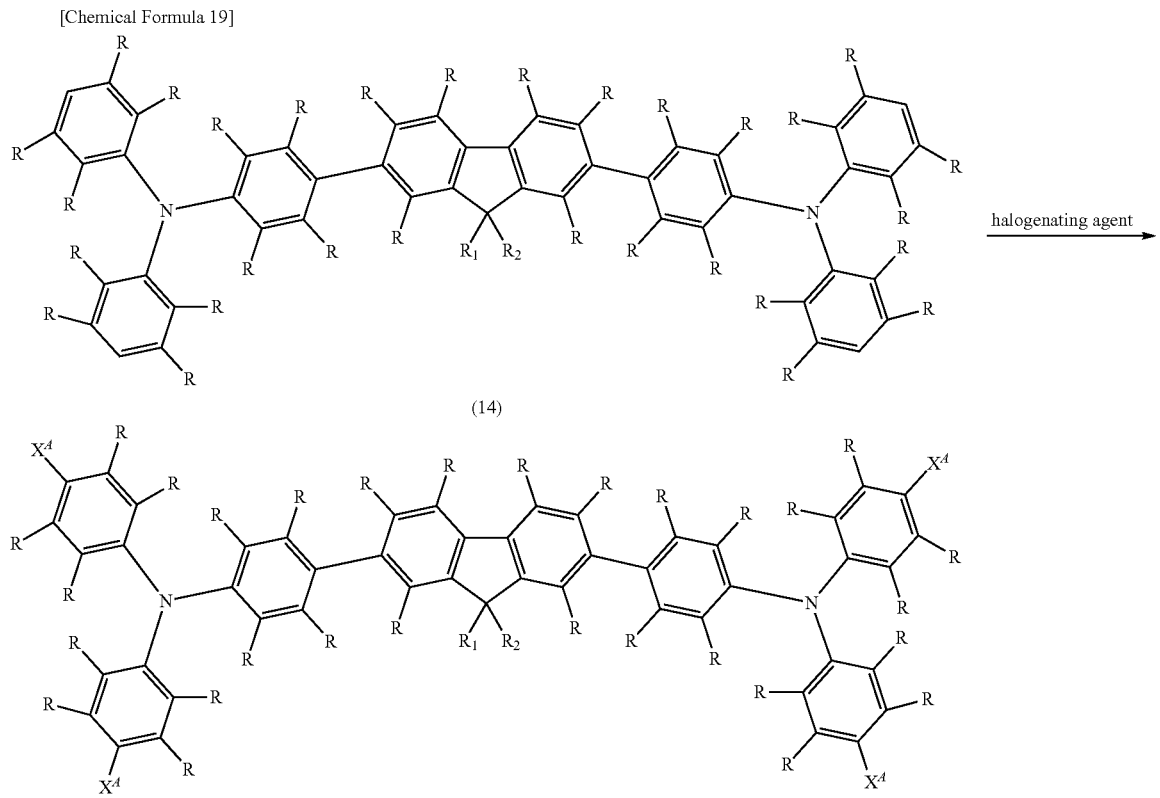

In the reaction shown in Scheme E, the charging ratio between the compound of formula (11) and the compound of formula (12), expressed as a molar ratio, is from about 1 to about 3 moles of the compound of formula (12) per mole of the compound of formula (11).

The catalyst used in the Scheme E reaction is exemplified by the above-mentioned palladium catalysts.

The solvent used in the reaction of Scheme E is exemplified by dimethylsulfoxide, N,N-dimethylformamide, N,N-dimethylacetamide, tetrahydrofuran, dioxane, acetonitrile and toluene. From the standpoint of the solubility and reactivity of the starting compounds, dioxane is preferred.

The reaction temperature may generally be from −50° C. to the boiling point of the solvent used, although the range of 0 to 100° C. is preferred. The reaction time is generally from 0.1 to 100 hours.

In the reaction shown in Scheme F, the charging ratio between the compound of formula (8) and the compound of formula (13), expressed as a molar ratio, is from about 2 to about 4 moles of the compound of formula (13) per mole of the compound of formula (8).

The catalyst used in the reaction shown in Scheme F is exemplified by the same catalysts as described in the reaction shown in Scheme C.

The reaction temperature may generally be from −50° C. to the boiling point of the solvent used, although the range of 0 to 140° C. is preferred. The reaction time is generally from 0.1 to 100 hours.

The halogenating agent and solvent used in the reaction shown in Scheme G may be the same as those described for the reaction shown in Scheme D. This halogenating agent is used in an amount, expressed as a molar ratio, of about 4 to about 6 moles per mole of the compound of formula (14).

The reaction temperature may generally be from −50° C. to the boiling point of the solvent used, although the range of 0 to 140° C. is preferred. The reaction time is generally from 0.1 to 100 hours.

Following completion of the reactions shown in the above schemes, the product may be used directly as is in the next step without purification, or purification may be carried out. When purification is carried out, the target compound may be obtained by carrying out such purification in the usual manner.

A fluorene derivative of formula (2') can be synthesized by reacting a compound of formula (15) with compounds of formulas (16-1) and (16-2) to synthesize an intermediate of formula (17) (Scheme H), and then reacting this with a compound of formula (12) in the presence of a catalyst (Scheme I). In a more specific example, a fluorene derivative of formula (2'') can be synthesized by reacting a compound of formula (15) with a compound of formula (16-1') to synthesize an intermediate of formula (17') (Scheme H'), and then reacting this with a compound of formula (12) in the presence of a catalyst (Scheme I'). In the schemes shown below, Ar, $X^A$, $X^B$, $R^c$, $R^3$ and $R^4$ are as defined above.

Scheme H

[Chemical Formula 20]

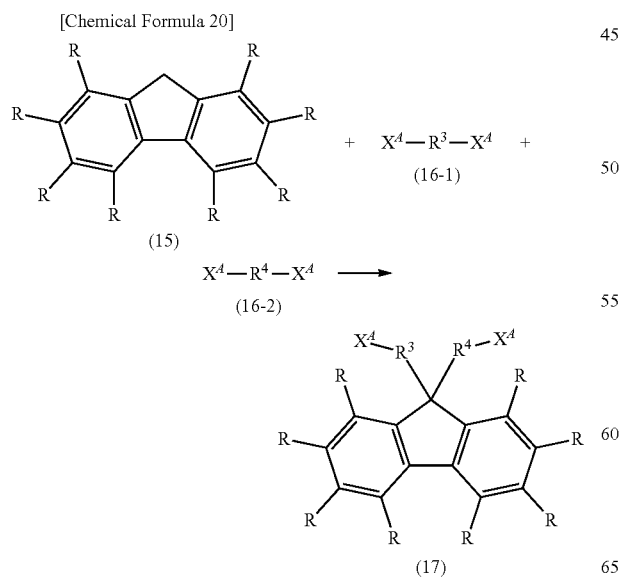

Scheme H'

[Chemical Formula 21]

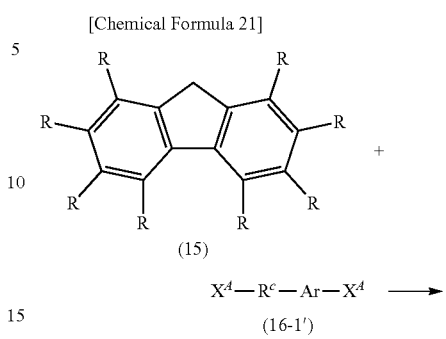

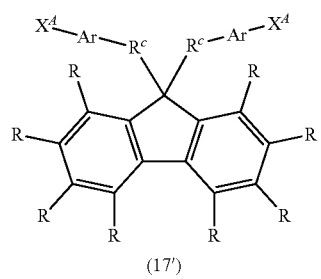

Scheme I

[Chemical Formula 22]

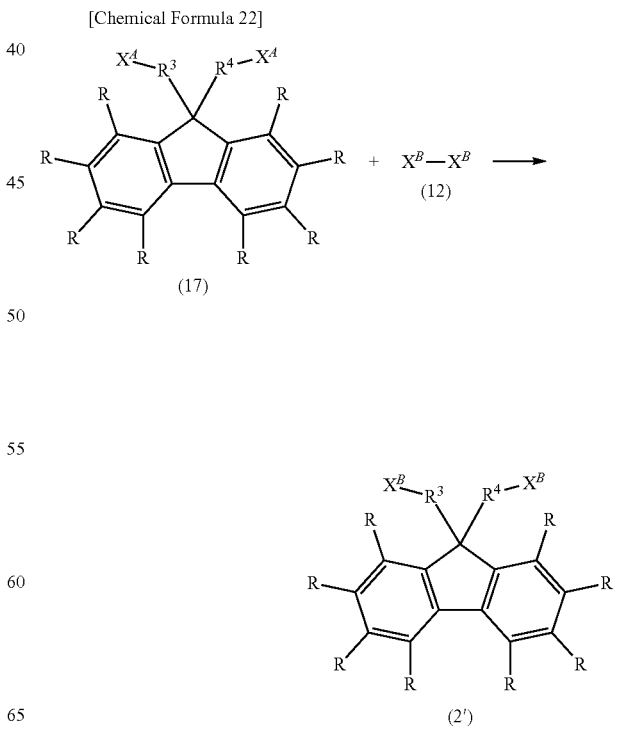

Scheme I'

[Chemical Formula 23]

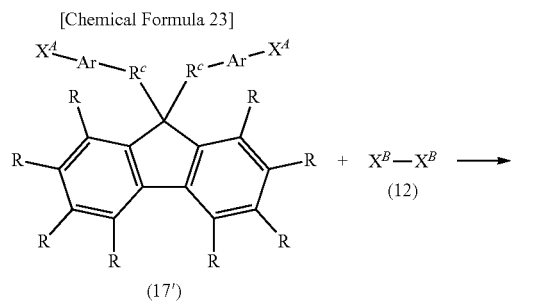

(17')

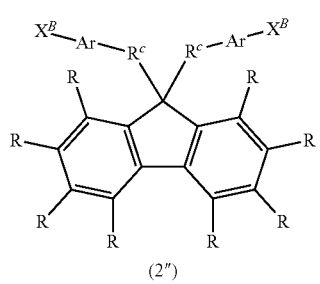

(2")

In the reaction shown in Scheme H, the charging ratio between the compound of formula (15) and the compounds of formulas (16-1) and (16-2), expressed as a molar ratio, is from about 1 to about 3 moles of the compounds of formulas (16-1) and (16-2) per mole of the compound of formula (15). In the reaction shown in Scheme H', the charging ratio between the compound of formula (15) and the compound of formula (16-1'), expressed as a molar ratio, is from about 1 to about 3 moles of the compound of formula (16-1') per mole of the compound of formula (15).

The solvents used in the reactions shown in Schemes H and H' are exemplified by dimethylsulfoxide, N,N-dimethylformamide, N,N-dimethylacetamide, tetrahydrofuran, dioxane, acetonitrile and toluene. From the standpoint of reactivity, tetrahydrofuran and N,N-dimethylformamide are preferred.

The reaction temperature may generally be from −50° C. to the boiling point of the solvent used, although the range of 0 to 140° C. is preferred. The reaction time is generally from 0.1 to 100 hours.

In the reaction shown in Scheme I, the charging ratio between the compound of formula (17) and the compound of formula (12), expressed as a molar ratio, is from about 1 to about 3 moles of the compound of formula (12) per mole of the compound of formula (17). In the reaction shown in Scheme I', the charging ratio between the compound of formula (17') and the compound of formula (12), expressed as a molar ratio, is from about 1 to about 3 moles of the compound of formula (12) per mole of the compound of formula (17).

The catalysts and solvents used in the reactions of Schemes I and I' are the same as those described for the reaction shown in Scheme E.

The reaction temperature may generally be from −50° C. to the boiling point of the solvent used, although the range of 0 to 140° C. is preferred. The reaction time is generally from 0.1 to 100 hours.

Following completion of the reactions shown in the above schemes, the product may be used directly as is in the next step without purification, or purification may be carried out. When purification is carried out, the target compound may be obtained by carrying out such purification in the usual manner.

A fluorene derivative of formula (3') can be synthesized by reacting a compound of formula (6) with compounds of formulas (18-1) and (18-2) to synthesize an intermediate of formula (19) (Scheme J), and then reacting this with the compound of formula (12) in the presence of a catalyst (Scheme K). In this scheme, $X^A$, $X^B$, $R^5$ and $R^6$ are as defined above.

Scheme J

[Chemical Formula 24]

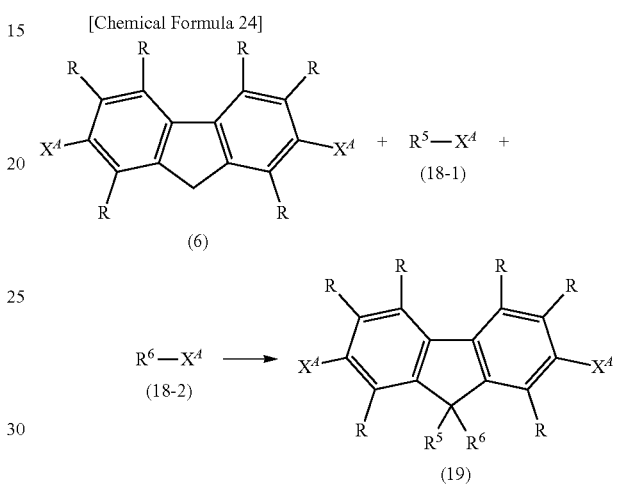

Scheme K

[Chemical Formula 25]

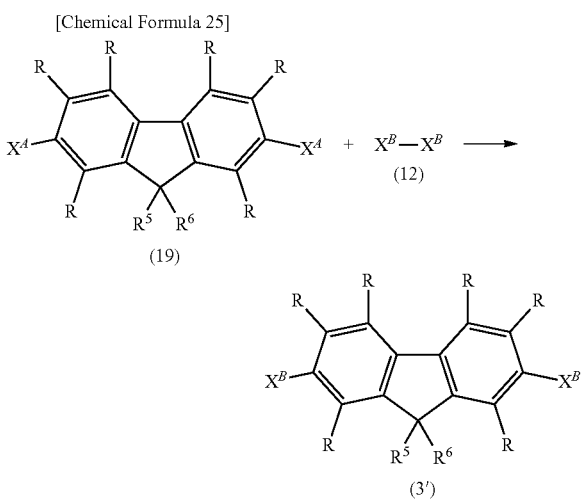

In the reaction shown in Scheme J, the charging ratio between the compound of formula (6) and the compounds of formulas (18-1) and (18-2), expressed as a molar ratio, is from about 1 to about 3 moles of the compounds of formulas (18-1) and (18-2) per mole of the compound of formula (6).

The solvent used in the reaction shown Scheme J is exemplified in the same way as described for the reaction shown in Scheme H.

In the reaction shown in Scheme K, the charging ratio between the compound of formula (19) and the compound of formula (12), expressed as a molar ratio, is from about 1 to about 3 moles of the compound of formula (12) per mole of the compound of formula (19).

The catalyst and solvent used in the reaction of Scheme K are exemplified in the same way as those described for the reaction shown in Scheme E.

Following completion of the reactions shown in the above schemes, the product may be used directly as is in the next step without purification, or purification may be carried out. When purification is carried out, the target compound may be obtained by carrying out such purification in the usual manner.

Typically, in the polymerization reactions for polymers of this invention, because it is possible to react a monomer of formula (1') with either a monomer of formula (2') or a monomer of formula (3'), and a monomer of formula (2') does not react with a monomer of formula (3'), the recurring units adjacent to recurring units of formula (1) are either recurring units of formula (2) or recurring units of formula (3). For the same reason, the recurring units adjacent to recurring units of formula (2) and the recurring units adjacent to recurring units of formula (3) are all recurring units of formula (1).

[Charge-Transporting Substance]

The fluorine atom-containing polymer of the invention can be suitably used as a charge-transporting substance. In the invention, "charge transportability" is synonymous with electrical conductivity, and is also synonymous with hole transportability. The charge-transporting substance may be one that itself has charge transportability, or may be one that has charge transportability when used together with a dopant. The charge-transporting varnish may be one that itself has charge transportability, or may be one where a solid film obtained therefrom has charge transportability.

[Charge-Transporting Varnish]

The charge-transporting varnish of the invention includes a charge-transporting substance consisting of the fluorine atom-containing polymer, a charge-transporting substance that contains no fluorine atoms, a dopant consisting of a heteropolyacid, and an organic solvent.

[Charge-Transporting Substance that Contains No Fluorine Atoms]

The charge-transporting substance that contains no fluorine atoms is exemplified by charge-transporting oligomers such as aniline derivatives, thiophene derivatives and pyrrole derivatives. The molecular weight of the charge-transporting oligomer is typically from 200 to 5,000. However, from the standpoint of preparing a varnish that gives thin films having a high charge transportability, the molecular weight is preferably at least 300, more preferably at least 400, and even more preferably at least 500. From the standpoint of preparing a uniform varnish that gives a thin film having a high flatness, the molecular weight is preferably 4,000 or less, more preferably 3,000 or less, and even more preferably 2,000 or less.

Of the above charge-transporting oligomers, taking into account the balance between the solubility in organic solvents and the charge transportability of the resulting thin film, aniline derivatives are preferred. Examples of aniline derivatives include the oligoaniline derivatives mentioned in JP-A 2002-151272, the oligoaniline compounds mentioned in WO 2004/105446, the oligoaniline compounds mentioned in WO 2008/032617, the oligoaniline compounds mentioned in WO 2008/032616 and the aryldiamine compounds mentioned in WO 2013/042623.

Aniline derivatives of formula (20) below can also be advantageously used.

[Chemical Formula 26]

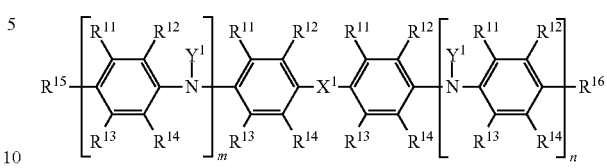

(20)

In formula (20), $X^1$ represents $-NY^1-$, $-O-$, $-S-$, $-(CR^{17}R^{18})_L-$ or a single bond. When m or n is 0, $X^1$ represents $-NY^1-$.

Each $Y^1$ is independently a hydrogen atom, an alkyl group of 1 to 20 carbon atoms, alkenyl group of 2 to 20 carbon atoms or alkynyl group of 2 to 20 carbon atoms which may be substituted with $Z^{11}$, or an aryl group of 6 to 20 carbon atoms or heteroaryl group of 2 to 20 carbon atoms which may be substituted with $Z^{12}$.

The alkyl group of 1 to 20 carbon atoms, alkenyl group of 2 to 20 carbon atoms, alkynyl group of 2 to 20 carbon atoms, aryl group of 6 to 20 carbon atoms and heteroaryl group of 2 to 20 carbon atoms are exemplified in the same way as above.

$R^{17}$ and $R^{18}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^{11}$, an aryl group of 6 to 20 carbon atoms or heteroaryl group of 2 to 20 carbon atoms which may be substituted with $Z^{12}$, or $-NHY^2$, $-NY^3Y^4$, $-C(O)Y^5$, $-OY^6$, $-SY^7$, $-SO_3Y^8$, $-C(O)OY^9$, $-OC(O)Y^{10}$, $-C(O)NHY^{11}$ or $-C(O)NY^{12}Y^{13}$.

$Y^2$ to $Y^{13}$ are each independently an alkyl group of 1 to 20 carbon atoms, alkenyl group of 2 to 20 carbon atoms or alkynyl group of 2 to 20 carbon atoms which may be substituted with $Z^{11}$, or an aryl group of 6 to 20 carbon atoms or heteroaryl group of 2 to 20 carbon atoms which may be substituted with $Z^{12}$.

$Z^{11}$ is a chlorine atom, a bromine atom, an iodine atom, a nitro group, a cyano group, an amino group, an aldehyde group, a hydroxyl group, a thiol group, a sulfonic acid group, a carboxyl group, or an aryl group of 6 to 20 carbon atoms or heteroaryl group of 2 to 20 carbon atoms which may be substituted with $Z^{13}$.

$Z^{12}$ is a chlorine atom, a bromine atom, an iodine atom, a nitro group, a cyano group, an amino group, an aldehyde group, a hydroxyl group, a thiol group, a sulfonic acid group, a carboxyl group, or an alkyl group of 1 to 20 carbon atoms, alkenyl group of 2 to 20 carbon atoms or alkynyl group of 2 to 20 carbon atoms which may be substituted with $Z^{13}$.

$Z^{13}$ is a chlorine atom, a bromine atom, an iodine atom, a nitro group, a cyano group, an amino group, an aldehyde group, a hydroxyl group, a thiol group, a sulfonic acid group, or a carboxyl group.

The alkyl, alkenyl, alkynyl, aryl and heteroaryl groups of $R^{17}$, $R^{18}$ and $Y^2$ to $Y^{13}$ are exemplified in the same way as above.

Of these, $R^{17}$ and $R^{18}$ are preferably hydrogen atoms or alkyl groups of 1 to 20 carbon atoms which may be substituted with $Z^{11}$, more preferably hydrogen atoms or methyl groups which may be substituted with $Z^{11}$, and most preferably both hydrogen atoms.

L is the number of groups represented by —$(CR^7R^{18})$—, this number being an integer of from 1 to 20, preferably from 1 to 10, more preferably from 1 to 5, even more preferably 1 or 2, and most preferably 1. When L is 2 or more, the plurality of $R^{17}$ groups may be mutually the same or different and the plurality of $R^{18}$ groups may likewise be mutually the same or different.

In particular, $X^1$ is preferably —$NY^1$— or a single bond. $Y^1$ is preferably a hydrogen atom or an alkyl group of 1 to 20 carbon atoms which may be substituted with $Z^{11}$, more preferably a hydrogen atom or a methyl group which may be substituted with $Z^{11}$, and most preferably a hydrogen atom.

In formula (20), $R^{11}$ to $R^{16}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^{11}$, an aryl group of 6 to 20 carbon atoms or heteroaryl group of 2 to 20 carbon atoms which may be substituted with $Z^{12}$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$ (wherein $Y^2$ to $Y^{13}$ are as defined above). These alkyl, alkenyl, alkynyl, aryl and heteroaryl groups are exemplified in the same way as above.

In particular, in formula (20), $R^{11}$ to $R^{14}$ are preferably hydrogen atoms, alkyl groups of 1 to 10 carbon atoms which may be substituted with $Z^{11}$, or aryl groups of 6 to 14 carbon atoms which may be substituted with $Z^{12}$; more preferably hydrogen atoms or alkyl groups of 1 to 10 carbon atoms which may be substituted with $Z^{11}$; and most preferably all hydrogen atoms.

$R^{15}$ and $R^{16}$ are preferably hydrogen atoms, alkyl groups of 1 to 10 carbon atoms which may be substituted with $Z^{11}$, aryl groups of 6 to 14 carbon atoms which may be substituted with $Z^{12}$, or diphenylamino groups which may be substituted with $Z^{12}$ (—$NY^3Y^4$ groups wherein $Y^3$ and $Y^4$ are phenyl groups which may be substituted with $Z^{12}$); more preferably hydrogen atoms or diphenylamino groups which may be substituted with $Z^{12}$; and even more preferably are both hydrogen atoms or diphenylamino groups.

Of these, combinations wherein $R^{11}$ to $R^{14}$ are hydrogen atoms or alkyl groups of 1 to 10 carbon atoms which may be substituted with $Z^{11}$, $R^{15}$ and $R^{16}$ are hydrogen atoms or diphenylamino groups which may be substituted with $Z^{12}$, $X^1$ is —$NY^1$— or a single bond, and $Y^1$ is a hydrogen atom or a methyl group are preferred; and combinations wherein $R^{11}$ to $R^{15}$ are hydrogen atoms, $R^{15}$ and $R^{16}$ are both hydrogen atoms or both diphenylamino groups, and $X^1$ is —NH— or a single bond are more preferred.

In formula (20), m and n are each independently integers of 0 or more and satisfy the condition $1 \leq m+n \leq 20$. However, taking into account the balance between the charge transportability of the resulting thin film and the solubility of the aniline derivative, they preferably satisfy the condition $2 \leq m+n \leq 8$, more preferably satisfy the condition $2 \leq m+n \leq 6$, and even more preferably satisfy the condition $2 \leq m+n \leq 4$.

In particular, in $Y^1$ to $Y^{13}$ and $R^{11}$ to $R^{18}$, $Z^{11}$ is preferably an aryl group of 6 to 20 carbon atoms which may be substituted with $Z^{13}$, more preferably a phenyl group which may be substituted with $Z^{13}$, and most preferably does not exist (i.e., is non-substituting).

$Z^{12}$ is preferably an alkyl group of 1 to 20 carbon atoms which may be substituted with $Z^{13}$, more preferably an alkyl group of 1 to 4 carbon atoms which may be substituted with $Z^{13}$, and most preferably does not exist (i.e., is non-substituting).

$Z^{13}$ most preferably does not exist (i.e., is non-substituting).

In $Y^1$ to $Y^{13}$ and $R^{11}$ to $R^{18}$, the number of carbon atoms on the alkyl, alkenyl and alkynyl groups is preferably 10 or less, more preferably 6 or less, and even more preferably 4 or less. The number of carbon atoms on the aryl and heteroaryl groups is preferably 14 or less, more preferably 10 or less, and even more preferably 6 or less.

Examples of methods for synthesizing the aniline derivative include, but are not particularly limited to, the methods described in *Bulletin of Chemical Society of Japan*, 67, pp. 1749-1752 (1994); *Synthetic Metals*, 84, pp. 119-120 (1997); *Thin Solid Films*, 520 (24), pp. 7157-7163 (2012); WO 2008/032617, WO 2008/032616, WO 2008/129947 and WO 2013/084664.

Illustrative examples of the aniline derivative of formula (20) include, but are not limited to, those of the following formulas. In the formulas below, DPA stands for a diphenylamino group, Ph stands for a phenyl group, and TPA stands for a p-(diphenylamino)phenyl group.

[Chemical Formula 27]

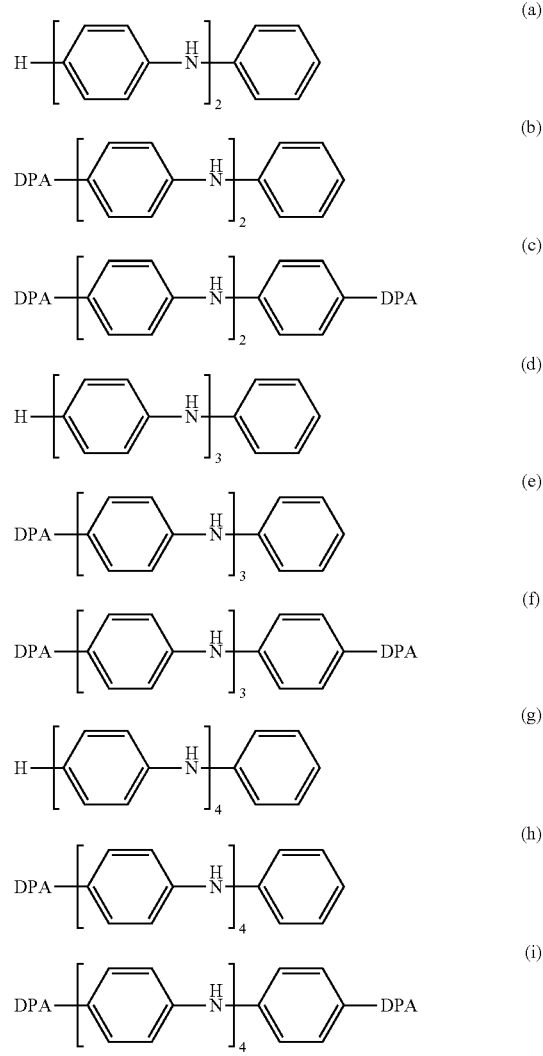

[Chemical Formula 28]

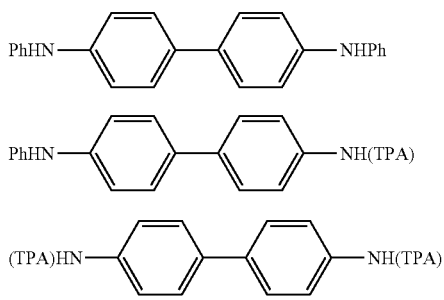

The content of charge-transporting substances in the varnish of the invention, from the standpoint of minimizing deposition of the charge-transporting substances, is preferably from about 0.1 to about 20 wt % based on the overall varnish. Also, in order to further increase the brightness characteristics of the resulting organic EL device, the charge-transporting substance consisting of a fluorine atom-containing polymer and the charge-transporting substance which does not contain fluorine atoms are used in a ratio therebetween, expressed as the mass ratio of the charge-transporting substance consisting of a fluorine atom-containing polymer with respect to unity (1) for the charge-transporting substance which does not contain fluorine atoms, of preferably from about 0.1 to about 5, more preferably from about 0.5 to about 3, and even more preferably from about 0.5 to about 1.

[Dopant]

The charge-transporting varnish of the invention includes as the dopant a heteropolyacid. As a result, there can be obtained a thin film of excellent charge-transportability which exhibits not only a high ability to accept holes from transparent electrodes such as indium-tin oxide (ITO) and indium-zinc oxide (IZO), but also a high ability to accept holes from metal anodes such as aluminum.

Figure 1B:
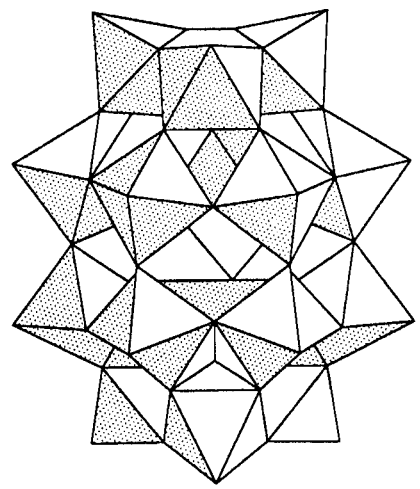
FIG. 1B shows a Dawson-type chemical structure.

"Heteropolyacid" refers to a polyacid having a structure in which a heteroatom is positioned at the center of the molecule—typically a Keggin-type chemical structure shown in FIG. 1A or a Dawson-type chemical structure shown in FIG. 1B, and which is obtained by the condensation of an isopolyacid that is an oxoacid of vanadium (V), molybdenum (Mo), tungsten (W) or the like with an oxoacid of a different element. Examples of such oxoacids of a different element include primarily oxoacids of silicon (Si), phosphorus (P) and arsenic (As).

Examples of heteropolyacids include phosphomolybdic acid, silicomolybdic acid, phosphotungstic acid, silicotungstic acid and phosphotungstomolybdic acid. These may be used singly, or two or more may be used in combination. The heteropolyacid used in this invention may be acquired as a commercial product or may be synthesized by a known method.

In particular, when the dopant consists of a single heteropolyacid, this heteropolyacid is preferably phosphotungstic acid or phosphomolybdic acid, and more preferably phosphotungstic acid. When the dopant consists of two or more heteropolyacids, at least one of the two or more heteropolyacids is preferably phosphotungstic acid or phosphomolybdic acid, and more preferably phosphotungstic acid.

Even a heteropolyacid having, in quantitative analysis such as elemental analysis, numbers for the elements which are higher or lower than in the structure indicated by the general formula may be used in this invention, provided it was acquired as a commercial product or was suitably synthesized according to a known method of synthesis.

For example, phosphotungstic acid is generally represented by the chemical formula $H_3(PW_{12}O_{40}) \cdot nH_2O$ and phosphomolybdic acid is generally represented by the chemical formula $H_3(PMo_{12}O_{40}) \cdot nH_2O$. In quantitative analysis, regardless of whether the numbers for the elements P (phosphorus), O (oxygen) and W (tungsten) or Mo (molybdenum) within these formulas are high or low, so long as the heteropolyacid was acquired as a commercial product or suitably synthesized by a known method of synthesis, it may be used in this invention. In such cases, the mass of the heteropolyacid specified in this invention refers not to the mass of pure phosphotungstic acid within the product of synthesis or the commercial product (phosphotungstic acid content), but rather, in the form that is available as a commercial product or the form that can be isolated by a known method of synthesis, to the total mass in a state that includes water of hydration and other impurities.

From the standpoint of reproducibly obtaining a charge-transporting thin film that provides a high brightness when used in organic EL devices, the heteropolyacid is included within the charge-transporting varnish of the invention in a mass ratio, relative to unity (1) for the charge-transporting substance which does not contain fluorine atoms, of preferably from about 2 to about 10, and more preferably from about 2.5 to about 9.0.

[Organic Solvent]

A high-solvency solvent capable of dissolving well the charge-transporting substance and dopant may be used as the organic solvent when preparing the charge-transporting varnish.

Examples of such high-solvency solvents include, but are not limited to, organic solvents such as cyclohexanone, N,N-dimethylformamide, N,N-dimethylacetamide, N-methylpyrrolidone and 1.3-dimethyl-2-imidazolidinone. These solvents may be used singly or two or more may be used in admixture. The amount of use thereof may be set to from 5 to 100 mass % of the total solvent used in the varnish.

It is preferable for the charge-transporting substance and the dopant to both be completely dissolved in this solvent.

In the present invention, at least one type of high-viscosity organic solvent having a viscosity at 25° C. of from 10 to 200 mPa·s, especially 35 to 150 mPa·s, and a boiling point at standard pressure (atmospheric pressure) of 50 to 300° C., especially 150 to 250° C., may be included in the varnish. By adding such a solvent, adjusting the viscosity of the varnish is easy, making it possible to prepare a varnish which reproducibly gives thin films of high flatness and is suitable for the method of application to be used.

Examples of high-viscosity organic solvents include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol.

The addition ratio of the high-viscosity organic solvent with respect to the overall solvent used in the varnish of the invention is preferably in a range within which the deposition of solids does not occur. An addition ratio of from 5 to 90 mass % is preferred, so long as solids do not deposit out.

In addition, another solvent may also be admixed in a ratio with respect to the overall solvent used in the varnish of from 1 to 90 mass %, and preferably from 1 to 50 mass %, for such purposes as to increase the wettability on a substrate, adjust the surface tension of the solvent, adjust the polarity, and adjust the boiling point.

Examples of such solvents include, but are not limited to, propylene glycol monomethyl ether, ethylene glycol monobutyl ether, diethylene glycol diethyl ether, diethylene glycol monomethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly or two or more may be used in admixture.

The viscosity of the inventive varnish, which is suitably set according to the thickness and other properties of the thin film to be produced and the solids concentration of the varnish, is typically from 1 to 50 mPa·s at 25° C. The solids concentration of the charge-transporting varnish in this invention, which is suitably set while taking into account such considerations as the viscosity and surface tension of the varnish and the thickness of the thin film to be formed, is typically from about 0.1 to about 10.0 mass %. In terms of increasing the coatability of the varnish, the solids concentration is preferably from 0.5 to 5.0 mass %, and more preferably from 1.0 to 3.0 mass %. As used herein, "solids" refers to the varnish ingredients exclusive of the organic solvent.

The method of preparing the varnish is exemplified by, but not particularly limited to, a method in which the charge-transporting substance consisting of the fluorine atom-containing polymer of the invention is first dissolved in a solvent, and the charge-transporting substance which does not contain fluorine atoms and the dopant consisting of a heteropolyacid are added one after another thereto; and a method in which a mixture of these substances is dissolved in the solvent.

In cases where there are a plurality of organic solvents, the charge-transporting substance consisting of the fluorine atom-containing polymer of the invention, the charge-transporting substance which does not contain fluorine atoms and the like may first be dissolved in a solvent that dissolves them well, after which the other solvent(s) may be added thereto. Alternatively, the charge-transporting substance consisting of the fluorine atom-containing polymer, the charge-transporting substance which does not contain fluorine atoms and the like may be dissolved one after the other or all at the same time in a mixed solvent formed of the plurality of organic solvents.

In this invention, from the standpoint of reproducibly obtaining thin films of high flatness, after the charge-transporting substance consisting of the fluorine atom-containing polymer of the invention, the charge-transporting substance which does not contain fluorine atoms and the like have been dissolved in the organic solvent, it is desirable for the charge-transporting varnish to be filtered using, for example, a submicron-order filter.

[Charge-Transporting Thin Film]

A charge-transporting thin film can be formed on a substrate by applying the charge-transporting varnish of the invention to a substrate, and baking the applied varnish.

Examples of methods for applying the varnish include, but are not limited to, dipping, spin coating, transfer printing, roll coating, brush coating, ink-jet printing, spraying and slit coating. It is preferable to adjust the viscosity and surface tension of the varnish according to the method of application.

When using the varnish of the invention, the baking atmosphere also is not particularly limited. A thin film having a uniform surface and a high charge transportability can be obtained not only in an open-air atmosphere, but even in inert gas such as nitrogen or in a vacuum.

The baking temperature is suitably set in the range of generally 100 to 260° C. while taking into account such factors as the intended use of the resulting thin film and the degree of charge transportability to be imparted to the thin film. When the thin film thus obtained is to be used as a functional single-layer film provided between the anode and the light-emitting layer of an organic EL device in a form that contacts both (i.e., a hole-injecting-and-transporting layer), the baking temperature is preferably from about 140 to about 250° C., and more preferably from about 150 to about 230° C.

During baking, a temperature change in two or more steps may be applied for such purposes as to achieve more uniform film formability or to induce the reaction to proceed on the substrate. Heating may be carried out using a suitable apparatus such as a hot plate or an oven.

The thickness of the charge-transporting thin film is not particularly limited, and can be set to from about 5 to about 200 nm when used in an organic EL device. When the charge-transporting thin film is to be used as a hole-injecting- and transporting layer, in order to increase the degree of phase separation between the two types of charge-transporting substances used in the invention and further increase the brightness characteristics and longevity characteristics of the organic EL device, the film thickness is preferably from 10 to 100 nm, more preferably from 20 to 50 nm, and even more preferably from 25 to 45 nm. Methods for changing the film thickness include, for example, changing the solids concentration in the varnish and changing the amount of solution on the substrate at the time of application.

[Organic EL Device]

The materials and method employed to fabricate organic light-emitting diode (OLED) devices using the charge-transporting varnish of the invention are exemplified by, but not limited to, those mentioned below.

The electrode substrate to be used is preferably cleaned beforehand by liquid washing with, for example, a cleaning agent, alcohol or pure water. When the substrate is an anode substrate, it is preferably subjected to surface treatment such as UV/ozone treatment or oxygen-plasma treatment just prior to use. However, surface treatment need not be carried out if the anode material is composed primarily of organic substances.

A method of fabricating an OLED device having a functional single-layer film (hole-injecting-and-transporting layer) consisting of a thin film obtained from the charge-transporting varnish of the invention is described below by way of illustration.

A functional single-layer film is formed on an electrode by applying the charge-transporting varnish of the invention to an anode substrate and carrying out baking by the method described above. The workpiece is then introduced into a vacuum deposition system, where a light-emitting layer, electron-transporting layer, electron-injecting layer and cathode metal are vapor-deposited thereon in this order to form the OLED device. Where necessary, an electron-blocking layer may be provided between the light-emitting layer and the hole-injecting-and-transporting layer.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having high charge transportability.

Examples of other metals making up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of light-emitting layer-forming materials include tris(8-quinolinolate) aluminum(II) ($Alq_3$), bis(8-quinolinolate) zinc(II) ($Znq_2$),
bis(2-methyl-8-quinolinolate)-4-(p-phenylphenolate) aluminum(III) (BAlq),
4,4'-bis(2,2-diphenylvinyl)biphenyl, 9,10-di(naphthalen-2-yl)anthracene,
2-t-butyl-9,10-di(naphthalen-2-yl)anthracene,
2,7-bis[9,9-di(4-methylphenyl)fluoren-2-yl]-9,9-di(4-methylphenyl)fluorene,
2-methyl-9,10-bis(naphthalen-2-yl)anthracene, 2-(9,9-spirobifluoren-2-yl)-9,9-spirobifluorene,
2,7-bis(9,9-spirobifluoren-2-yl)-9,9-spirobifluorene,
2-[9,9-di(4-methylphenyl)fluoren-2-yl]-9,9-di(4-methylphenyl)fluoren,
2,2'-dipyrenyl-9,9-spirobifluorene, 1,3,5-tris(pyren-1-yl)benzene,
9,9-bis[4-(pyrenyl)phenyl]-9H-fluorene, 2,2'-bi(9,10-diphenylanthracene),
2,7-dipyrenyl-9,9-spirobifluorene, 1,4-di(pyren-1-yl)benzene, 1,3-di(pyren-1-yl)benzene,
6,13-di(biphenyl-4-yl)pentacene, 3,9-di(naphthalen-2-yl)perylene,
3,10-di(naphthalen-2-yl)perylene, tris[4-(pyrenyl)phenyl]amine,
10,10'-di(biphenyl-4-yl)-9,9'-bianthracene,
N,N'-di(naphthalen-1-yl)-N,N'-diphenyl[1,1':4',1":4",1"'-quaterphenyl]-4,4"'-diamine,
4,4'-di[10-(naphthalen-1-yl)anthracen-9-yl]biphenyl,
dibenzo{[f,f']-4,4',7,7'-tetraphenyl}diindeno[1,2,3-cd:1',2',3'-lm]perylene,
1-(7-(9,9'-bianthracen-10-yl)-9,9-dimethyl-9H-fluoren-2-yl)pyrene,
1-(7-(9,9'-bianthracen-10-yl)-9,9-dihexyl-9H-fluoren-2-yl)pyrene,
1,3-bis(carbazol-9-yl)benzene, 1,3,5-tris(carbazol-9-yl)benzene,
4,4',4"-tris(carbazol-9-yl)triphenylamine, 4,4'-bis(carbazol-9-yl)biphenyl (CBP),
4,4'-bis(carbazol-9-yl)-22'-dimethylbiphenyl, 2,7-bis(carbazol-9-yl)-9,9-dimethylfluorene,
2,2',7,7'-tetrakis(carbazol-9-yl)-9,9-spirobifluorene,
2,7-bis(carbazol-9-yl)-9,9-di(p-tolyl)fluorene, 9,9-bis[4-(carbazol-9-yl)phenyl]fluorene,
2,7-bis(carbazol-9-yl)-9,9-spirobifluorene, 1,4-bis(triphenylsilyl)benzene,
1,3-bis(triphenylsilyl)benzene,
bis(4-N,N-diethylamino-2-methylphenyl)-4-methylphenylmethane,
2,7-bis(carbazol-9-yl)-9,9-dioctylfluorene,
4,4"-di(triphenylsilyl)-p-terphenyl, 4,4'-di(triphenylsilyl)biphenyl,
9-(4-t-butylphenyl)-3,6-bis(triphenylsilyl)-9H-carbazole,
9-(4-t-butylphenyl)-3,6-ditrityl-9H-carbazole,
9-(4-t-butylphenyl)-3,6-bis(9-(4-methoxyphenyl)-9H-fluoren-9-yl)-9H-carbazole,
2,6-bis(3-(9H-carbazol-9-yl)phenyl)pyridine,
triphenyl(4-(9-phenyl-9H-fluoren-9-yl)phenyl)silane,
9,9-dimethyl-N,N-diphenyl-7-(4-(1-phenyl-1H-benzo[d]imidazol-2-yl)phenyl-9H-fluoren-2-amine,
3,5-bis(3-(9H-carbazol-9-yl)phenyl)pyridine,
9,9-spirobifluoren-2-yldiphenylphosphine oxide,
9,9'-(5-triphenylsilyl)-1,3-phenylene)bis(9H-carbazole),
3-(2,7-bis(diphenylphosphoryl)-9-phenyl-9H-fluoren-9-yl)-9-phenyl-9H-carbazole,
4,4,8,8,12,12-hexa(p-tolyl)-4H-8H-12H-12C-azadibenzo[cd,mn]pyrene,
4,7-di(9H-carbazol-9-yl)-1,10-phenanthroline, 2,2'-bis(4-(carbazol-9-yl)phenyl)biphenyl,
2,8-bis(diphenylphosphoryl)dibenzo[b,d]thiophene, bis(2-methylphenyl)diphenylsilane,
bis[3,5-di(9H-carbazol-9-yl)phenyl]diphenylsilane,
3,6-bis(carbazol-9-yl)-9-(2-ethylhexyl)-9H-carbazole,
3-(diphenylphosphoryl)-9-(4-(diphenylphosphoryl)phenyl)-9H-carbazole and
3,6-bis[(3,5-diphenyl)phenyl]-9-phenylcarbazole. The light-emitting layer may be formed by co-depositing any of these materials with a light-emitting dopant.

Specific examples of light-emitting dopants include
3-(2-benzothiazolyl)-7-(diethylamino)coumarin,
2,3,6,7-tetrahydro-1,1,7,7-tetramethyl-1H,5H,11H-10-(2-benzothiazolyl)quinolidino-[9,9a,1gh]coumarin,
quinacridone, N,N'-dimethylquinacridone, tris(2-phenylpyridine) iridium(III) ($Ir(ppy)_3$),
bis(2-phenylpyridine)(acetylacetonate) iridium(HT) ($Ir(ppy)_2(acac)$),
tris[2-(p-tolyl)pyridine]iridium(III) ($Ir(mppy)_3$), 9,10-bis[N,N-di(p-tolyl)amino]anthracene,
9,10-bis[phenyl(m-tolyl)amino]anthracene,
bis[2-(2-hydroxyphenyl)benzothiazolate] zinc(II),
$N^{10},N^{10},N^{10'},N^{10'}$-tetra(p-tolyl)-9,9'-bianthracene-10,10'-diamine,
$N^{10},N^{10},N^{10'},N^{10'}$-tetraphenyl-9,9'-bianthracene-10,10'-diamine,
$N^{10}N^{10'}$-diphenyl-$N^{10},N^{10'}$-dinaphthalenyl-9,9'-bianthracene-10,10'-diamine,
4,4'-bis(9-ethyl-3-carbazovinylene)-1,1'-biphenyl, perylene, 2,5,8,11-tetra-t-butylperylene,
1,4-bis[2-(3-N-ethylcarbazolyl)vinyl]benzene, 4,4'-bis[4-(di-p-tolylamino)styryl]biphenyl,
4-(di-p-tolylamino)-4'-[(di-p-tolylamino)styryl]stilbene,
bis[3,5-difluoro-2-(2-pyridyl)phenyl-(2-carboxypyridyl)] iridium(III),
4,4'-bis[4-(diphenylamino)styryl]biphenyl,
bis(2,4-difluorophenylpyridinato)tetrakis(1-pyrazolyl)borate iridium(III),
N,N'-bis(naphthalen-2-yl)-N,N'-bis(phenyl)tris(9,9-dimethylfluorenylene),
2,7-bis{2-[phenyl(m-tolyl)amino]-9,9-dimethylfluoren-7-yl}-9,9-dimethylfluorene,
N-(4-((E)-2-(6((E)-4-(diphenylamino)styryl)naphthalen-2-yl)vinyl)phenyl)-N-phenylbenzenamine,
fac-iridium(III) tris(1-phenyl-3-methylbenzimidazolin-2-ylidene-$C,C^2$),
mer-iridium(III) tris(1-phenyl-3-methylbenzimidazolin-2-ylidene-$C,C^2$),
2,7-bis[4-(diphenylamino)styryl]-9,9-spirobifluorene,
6-methyl-2-(4-(9-(4-(6-methylbenzo[d]thiazol-2-yl)phenyl)anthracen-10-yl)phenyl)-benzo[d]thiazole, 1,4-di[4-(N,N-diphenyl)amino]styrylbenzene, 14-bis(4-(9H-carbazol-9-yl)styryl)benzene,
(E)-6-(4-(diphenylamino)styryl)-N,N-diphenylnaphthlen-2-amine,
bis(2,4-difluorophenylpyridinato)(5-(pyridin-2-yl)-1H-tetrazolate) iridium(III),
bis(3-trifluoromethyl-5-(2-pyridyl)pyrazole)((2,4-difluorobenzyl)diphenylphosphinate) iridium(III),
bis(3-trifluoromethyl-5-(2-pyridyl)pyrazolate)(benzyldphenylphosphinate) iridium(III),
bis(1-(2,4-difluorobenzyl)-3-methylbenzimidazolium)(3-(trifluoromethyl)-5-(2-pyridyl)-1,2,4-triazolate) iridium (III),
bis(3-trifluoromethyl-5-(2-pyridyl)pyrazolate)(4',6'-difluorophenylpyrdinate) iridium(III),
bis(4',6'-difluorophenylpyridinato)(3,5-bis(trifluoromethyl)-2-(2'-pyridyl)pyrrolate) iridium(III),
bis(4',6'-difluorophenylpyridinato)(3-(trifluoromethyl)-5-(2-pyridyl)-1,2,4-triazolate) iridium (III),
(Z)-6-mesityl-N-(6-mesitylquinoline-2(1H)-ylidene)quinoline-2-amine-$BF_2$,
(E)-2-(2-(4-(dimethylamino)styryl)-6-methyl-4H-pyran-4-ylidene)malononitrile,
4 (dicyanomethylene)-2-methyl-6-julolidyl-9-enyl-4-H-pyran,
4-(dicyanomethylene)-2-methyl-6-(1,1,7,7-tetramethyljulolidyl-9-enyl)-4H-pyran,
4-(dicyanomethylene)-2-t-butyl-6-(1,1,7,7-tetramethyljulolidin-4-ylvinyl)-4H-pyran,
tris(dibenzoylmethane)phenanthroline europium(III), 5,6,11,12-tetraphenylnaphthacene,
bis(2-benzo[b]thiophen-2-yl-pyridine)(acetylacetonate) iridium(III),
tris(1-phenylisoquinoline) iridium(III),
bis(1-phenylisoquinoline)(acetylacetonate) iridium(III),
bis[1-(9,9-dimethyl-9H-fluoren-2-yl)isoquinoline](acetylacetonate) iridium(III),
bis[2-(9,9-dimethyl-9H-fluoren-2-yl)quinoline](acetylacetonate) iridium(III),
tris[4,4'-di-t-butyl-(2,2')-bipyridine] ruthenium(III)-bis(hexafluorophosphate),
tris(2-phenylquinoline) iridium(III), bis(2-phenylquinoline)(acetylacetonate) iridium(III),
2,8-di-t-butyl-5,11-bis(4-t-butylphenyl)-6,12-diphenyltetracene,
bis(2-phenylbenzothiazolate)(acetylacetonate) iridium(III),
platinum 5,10,15,20-tetraphenyltetrabenzoporphyrin,
osmium(II) bis(3-trifluoromethyl-5-(2-pyridine)pyrazolate) dimethylphenylphosphine,
osmium(II) bis(3-trifluoromethyl)-5-(4-t-butylpyridyl)-1,2,4-triazolate)diphenylmethyl-phosphine,
osmium(II) bis(3-(trifluoromethyl)-5-(2-pyridyl)-1,2,4-triazole)dimethylphenylphosphine,
osmium(II) bis(3-(trifluoromethyl)-5-(4-t-butylpyridyl)-1,2,4-triazolate)dimethylphenyl-phosphine,
bis[2-(4-n-hexylphenyl)quinoline](acetylacetonate) iridium (III),
tris[2-(4-n-hexylphenyl)quinoline] iridium(III), tris[2-phenyl-4-methylquinoline] iridium(III),
bis(2-phenylquinoline)(2-(3-methylphenyl)pyridinate) iridium(III),
bis(2-(9,9-diethylfluoren-2-yl)$_1$-phenyl-H-benzo[d]imidazolato)(acetylacetonate) iridium(III),
bis(2-phenylpyridine)(3-(pyridin-2-yl)-2H-chromen-9-onate) iridium(III),
bis(2-phenylquinoline)(2,2,6,6-tetramethylheptane-3,5-dionate) iridium(III), bis(phenylisoquinoline)(2,2,6,6-tetramethylheptane-3,5-dionate) iridium(III),
iridium(III) bis(4-phenylthieno[3,2-c]pyridinato-$N,C^2$) acetylacetonate,
(E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)malononitrile,
bis(3-trifluoromethyl-5-(1-isoquinolyl)pyrazolate)(methyldiphenylphosphine) ruthenium,
bis[(4-n-hexylphenyl)isoquinoline](acetylacetonate) iridium(III),
platinum(II) octaethylporphin,
bis(2-methyldibenzo[f,h]quinoxaline)(acetylacetonate) iridium(III) and
tris[(4-n-hexylphenyl)isoquinoline] iridium(III).

Specific examples of electron-transporting layer/hole-blocking layer-forming materials include lithium 8-hydroxyquinolinate,
2,2',2"-(1,3,5-benzinetriyl)-tris(1-phenyl-1-H-benzimidazole),
2-(4-biphenyl)-5-(4-t-butylphenyl)-1,3,4-oxadiazole,
2,9-dimethyl-4,7-diphenyl-1,10-phenanthroline, 4,7-diphenyl-1,10-phenanthroline,
bis(2-methyl-8-quinolinolate)-4-(phenylphenolato)aluminum,
1,3-bis[2-(2,2'-bipyridin-6-yl)-1,3,4-oxadiazo-5-yl]benzene,
6,6'-bis[5-(biphenyl-4-yl)-1,3,4-oxadiazo-2-yl]-2,2'-bipyridine,
3-(4-biphenyl)-4-phenyl-5-t-butylphenyl-1,2,4-triazole,
4-(naphthalen-1-yl)-3,5-diphenyl-4H-1,2,4-triazole,
2,9-bis(naphthalen-2-yl)-4,7-diphenyl-1,10-phenanthroline,
2,7-bis[2-(2,2'-bipyridin-6-yl)-1,3,4-oxadiazo-5-yl]-9,9-dimethylfluorene,
1,3-bis[2-(4-t-butylphenyl)-1,3,4-oxadiazo-5-yl]benzene,
tris(2,4,6-trimethyl-3-(pyridin-3-yl)phenyl)borane,
1-methyl-2-(4-(naphthalen-2-yl)phenyl)-1H-imidazo[4,5f][1,10]phenanthroline,
2-(naphthalen-2-yl)-4,7-diphenyl-1,10-phenanthroline, phenyldipyrenylphosphine oxide,
3,3',5,5'-tetra[(m-pyridyl)phen-3-yl]biphenyl, 1,3,5-tris[(3-pyridyl)phen-3-yl]benzene,
4,4'-bis(4,6-diphenyl-1,3,5-triazin-2-yl)biphenyl,
1,3-bis[3,5-di(pyridin-3-yl)phenyl]benzene, bis(10-hydroxybenzo[h]quinolinato)beryllium,
diphenylbis(4-(pyridin-3-yl)phenyl)silane and 3,5-di(pyren-1-yl)pyridine.

Examples of electron-injecting layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, lithium acetylacetonate (Li(acac)), lithium acetate and lithium benzoate.

Examples of cathode materials include aluminum, magnesium-silver alloys, aluminum-lithium alloys, lithium, sodium, potassium and cesium.

An example of an electron-blocking layer-forming material is tris(phenylpyrazole) iridium.

Processes for fabricating polymer LED (PLED) devices using the charge-transporting varnish of the invention, although not particularly limited, are exemplified by the following method.

A PLED device having a functional single-layer film (hole-injecting-and-transporting layer) consisting of a thin film obtained from the charge-transporting varnish of the invention can be fabricated by, in the production of an OLED device as described above, forming a light-emitting polymer layer instead of carrying out vacuum deposition operations for a light-emitting layer, an electron-transporting layer and an electron-injecting layer. Specifically, the charge-transporting varnish of the invention is applied to an anode substrate, thus forming a functional single-layer film by the above method. A light-emitting polymer layer is formed thereon, following which a cathode is vapor-deposited on top, thereby forming the PLED device.

The cathode and anode materials used here may be similar to those used when producing an OLED device as described above, and similar cleaning treatment and surface treatment may be carried out.

The method of forming the light-emitting polymer layer is exemplified by a film-forming method in which a solvent is added to a light-emitting polymer material, or to the material obtained by adding thereto a dopant substance, thereby dissolving or uniformly dispersing the materials, following which the resulting solution or dispersion is applied to the functional single-layer film and is subsequently baked.

Specific examples of light-emitting polymer materials include polyfluorene derivatives such as poly(9,9-dialkyl-fluorene) (PDAF), poly(phenylene vinylene) derivatives such as poly(2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Examples of the solvent include toluene, xylene and chloroform. Examples of the method of dissolution or uniform dispersion include stirring, stirring under applied heat, and ultrasonic dispersion.

The method of application is exemplified by, but not particularly limited to, inkjet printing, spraying, dipping, spin coating, transfer printing, roll coating and brush coating. Application is preferably carried out in an inert gas atmosphere such as nitrogen or argon.

Examples of the baking method include methods that involve heating in an oven or on a hot plate, either within an inert gas atmosphere or in a vacuum.

To prevent deterioration of the device characteristics, the organic EL device of the invention may be sealed in the usual manner with, if necessary, a desiccant or the like.

EXAMPLES

Synthesis Examples, Working Examples and Comparative Examples are given below to more concretely illustrate the invention, although the invention is not limited by these Examples. The equipment used was as follows.
(1) $^1$H-NMR Measurement: ECX-300, from JEOL Ltd.
(2) LC/MS: ZQ 2000, from Waters Corporation; TripleTOF 5600+, from AB Sciex
(3) MALDI-TOF-MS: Autoflex II SmartBeam, from Bruker Daltonics
(4) Substrate Cleaning: Substrate cleaning machine (reduced-pressure plasma system), from Choshu Industry Co., Ltd.
(5) Varnish Coating: MS-A100 Spin Coater, from Mikasa Co., Ltd.
(6) Film Thickness Measurement:
  Surfcorder ET-4000 microfigure measuring instrument, from Kosaka Laboratory, Ltd.
(7) GPC Measurement: Shimadzu Corporation system
  (columns: SHODEX GPC KF-804L+GPC KF-805L; column temperature: 40° C.; detector: UV detector (254 nm) and RI detector, eluant: THF; column flow rate: 1.0 ml/min)
(8) EL Device Fabrication:
  C-E2L1G1-N Multifunction Vapor Deposition System, from Choshu Industry Co., Ltd.
(9) Measurement of Brightness, etc. of EL Device:
  I-V-L Measurement System from Tech World, Inc.

[1] Synthesis of Compounds

[Synthesis Example 1] Synthesis of Compound 1

[Chemical Formula 30]

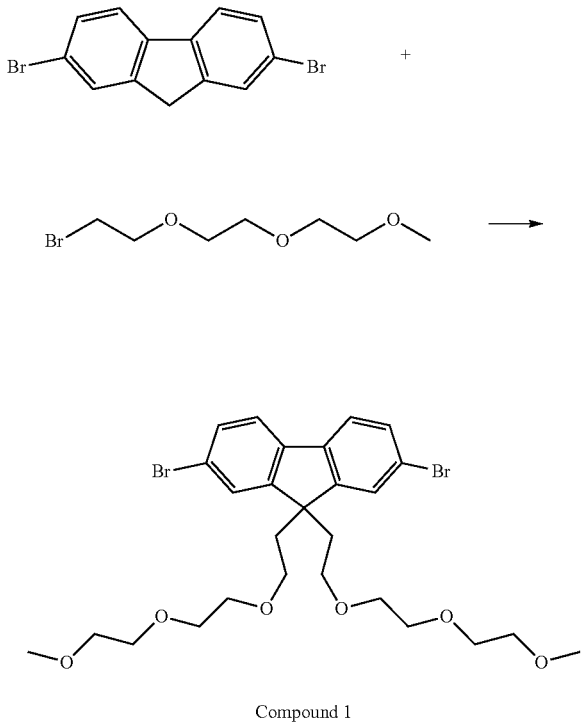

Compound 1

Potassium hydroxide (5.61 g, 100 mmol), potassium iodide (0.33 g, 2 mmol) and diethylene glycol 2-bromoethyl methyl ether (9.99 g, 44 mmol) were added to a dimethyl-sulfoxide suspension (130 mL) of 2,7-dibromofluorene (6.48 g, 20 mmol), and the system was stirred at room temperature for 24 hours. Following reaction completion, the system was cooled to 0° C., water (120 mL) was added, and neutralization was carried out with hydrochloric acid. The crude product obtained by extracting the organic layer with ethyl acetate, drying over magnesium sulfate and concentration was purified by silica gel column chromatography (eluate, hexane/ethyl acetate (4/1→3/1→2/1)), giving 8.30 g (yield, 67%) of Compound 1 as a white solid. The $^1$H-NMR and LC/MS results were as follows.

$^1$H-NMR (300 MHz, CDCl$_3$):

δ 2.33 (app t, J=7.8 Hz, 4H), 2.78 (app t, J=7.8 Hz, 4H), 3.19-3.22 (m, 4H), 3.35 (s, 6H), 3.37-3.41 (m, 4H), 3.50-3.52 (m, 8H), 7.46 (dd, J=1.8, 8.4 Hz, 2H), 7.51 (d, J=8.4 Hz, 2H), 7.53 (d, J=1.8 Hz, 2H).

LC/MS (ESI$^+$) m/z; 634 [M+NH$_4$]$^+$.

[Synthesis Example 2] Synthesis of Compound 2

[Chemical Formula 31]

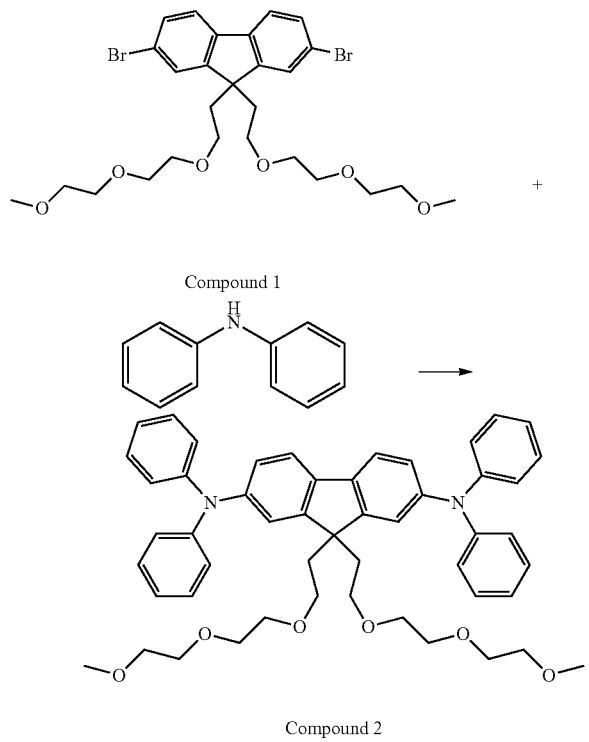

Palladium acetate (40.4 mg, 0.18 mmol), t-BuONa (3.81 g, 40 mmol) and [(t-Bu)$_3$PH]BF$_4$ (104 mg, 0.36 mmol) were added to a toluene solution (56 mL) of diphenylamine (4.61 g, 27 mmol) and Compound 1 (5.60 g, 9 mmol), and the system was flushed with nitrogen, then heated at 80° C. for 3 hours. Following reaction completion, the crude product obtained by Celite filtration and concentration of the filtrate was purified by silica gel column chromatography (eluate: hexane/ethyl acetate (2/1→1/1→1/2)), giving 1.17 g (16% yield) of Compound 2 as a light-brown solid. The $^1$H-NMR and LC/MS results were as follows.

$^1$H-NMR (300 MHz, CDCl$_3$):
δ 2.13 (app t, J=7.2 Hz, 4H), 2.88 (app t, J=7.2 Hz, 4H), 3.28-3.31 (m, 4H), 3.34 (s, 6H), 3.45-351 (m, 8H), 3.54-3.58 (m, 4H), 6.98-7.11 (m, 16H), 7.22-7.27 (m, 8H), 7.44 (d, J=8.1 Hz, 2H).
LC/MS (ESI$^+$) m/z; 794 [M+H]$^+$.

[Synthesis Example 3] Synthesis of Compound 3

[Chemical Formula 32]

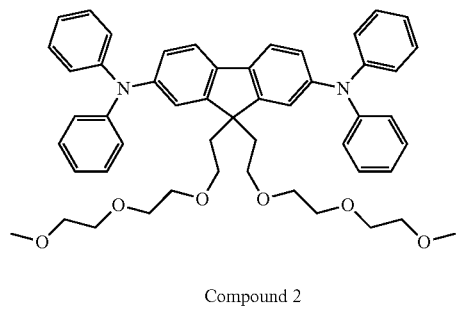

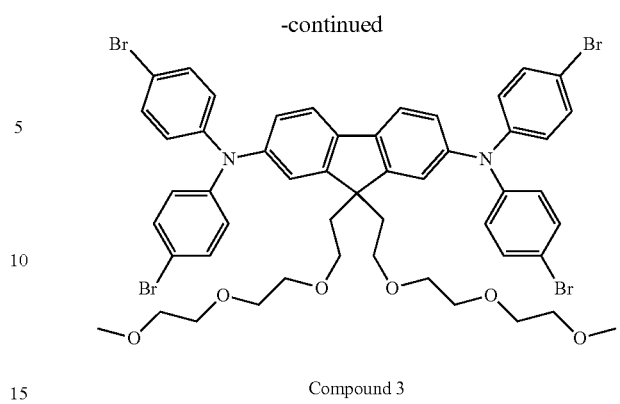

N-bromosuccinimide (2.73 g, 15.4 mmol) was added at 0° C. to a DMF solution (58 mL) of Compound 2 (2.90 g, 3.7 mmol), following which the system was stirred at room temperature for 1 hour. Following reaction completion, water (58 mL) was added at 0° C. and the organic layer was extracted with ethyl acetate. The crude product obtained by drying the extract over sodium sulfate and concentration was purified by silica gel column chromatography (eluate: hexane/ethyl acetate (4→1⁄3/1)), giving 3.95 g (93% yield) of Compound 3 as a white solid. The $^1$H-NMR and LC/MS results were as follows.

$^1$H-NMR (300 MHz, CDCl$_3$):
δ 2.14 (app t, J=7.2 Hz, 4H), 2.86 (app t, J=7.2 Hz, 4H), 3.26-333 (m, 4H), 3.35 (s, 6H), 3.41-3.57 (m, 12H), 6.83-7.05 (m, 12H), 7.25-7.47 (m, 10H).
LC/MS (ESI$^+$) m/z; 1131 [M+Na]$^+$.

[Synthesis Example 4] Synthesis of Compound 4

[Chemical Formula 33]

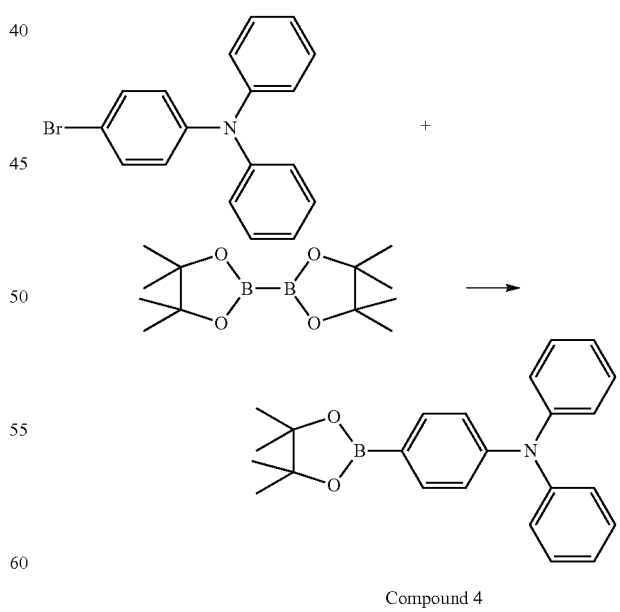

Potassium acetate (7.85 g, 80 mmol) and a dichloromethane adduct of PdCl$_2$(dppf) (0.65 g, 0.8 mmol) were added to a 1,4-dioxane solution (100 mL) of 4-bromotriphenylamine (13.0 g, 40 mmol) and bis(pinacolato)diboron (11.2 g, 44 mol), and the system was flushed with nitrogen, then heated at 100° C. for 2 hours. Following reaction completion, the crude product obtained by Celite filtration and concentration of the filtrate was purified by silica gel column chromatography (eluate:hexane/ethyl acetate (9/1)), giving 14.9 g (100% yield) of Compound 4 as a light-yellow solid. The $^1$H-NMR and LC/MS results were as follows.

$^1$H-NMR (300 MHz, CDCl$_3$):

δ 1.33 (s, 12H), 7.01-7.12 (m, 8H), 7.23-7.28 (m, 4H), 7.66 (d, J=8.7 Hz, 2H).

LC/MS (ESI$^+$) m/z; 372 [M+H]$^+$.

[Synthesis Example 5] Synthesis of Compound 5

[Chemical Formula 34]

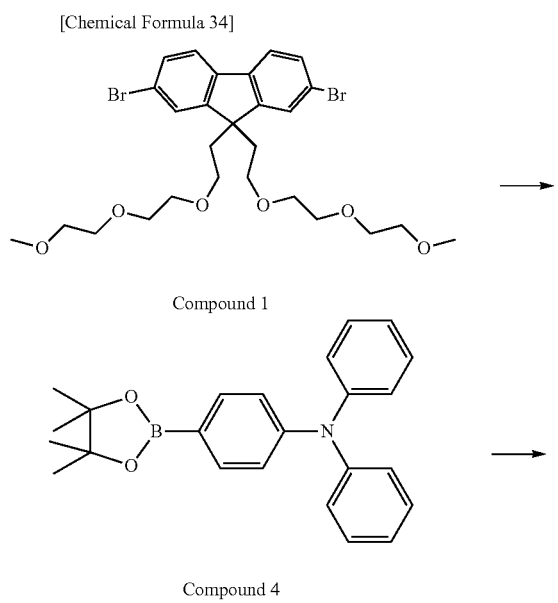

Compound 1

Compound 4

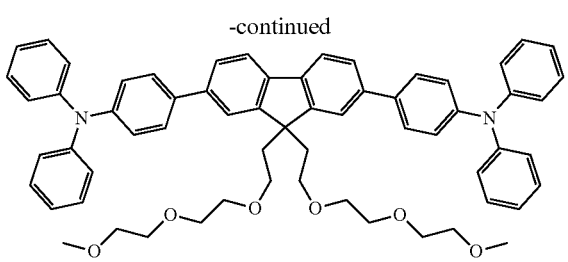

Compound 5

Methyl tri-n-octylammonium chloride (1.01 g, 2.5 mmol), Pd(PPh$_3$)$_4$ (462 mg, 0.4 mmol) and a 2 mol/L aqueous solution of sodium carbonate (20 mL, 40 mmol) were added to a toluene solution (123 mL) of Compound 1 (6.16 g, 10 mmol) and Compound 4 (8.17 g, 22 mmol), and the system was refluxed under heating for 4 hours. Following reaction completion, 1 mol/L hydrochloric acid (40 mL) was added, and the organic layer was extracted with ethyl acetate and dried over magnesium sulfate. The crude product obtained by Celite filtration and concentration of the filtrate was purified by silica gel column chromatography (eluate: hexane/ethyl acetate (4/1→2/1→1/1)), giving 7.74 g of a yellow liquid containing Compound 5 as the chief product. The $^1$H-NMR and LC/MS results were as follows.

$^1$H-NMR (300 MHz, CDCl$_3$):

δ 2.45 (app t, J=7.2 Hz, 4H), 2.84 (app t, J=7.2 Hz, 4H), 3.20-3.23 (m, 4H), 3.29 (s, 6H), 3.37-3.50 (m, 12H), 7.02-7.07 (m, 4H), 7.14-7.19 (m, 12H), 7.24-7.31 (m, 8H), 7.53-7.61 (m, 8H), 7.72 (d, J=8.1 Hz, 2H).

LC/MS (ESI$^+$) m/z; 963 [M+NH$_4$]$^+$.

[Synthesis Example 6] Synthesis of Compound 6

[Chemical Formula 35]

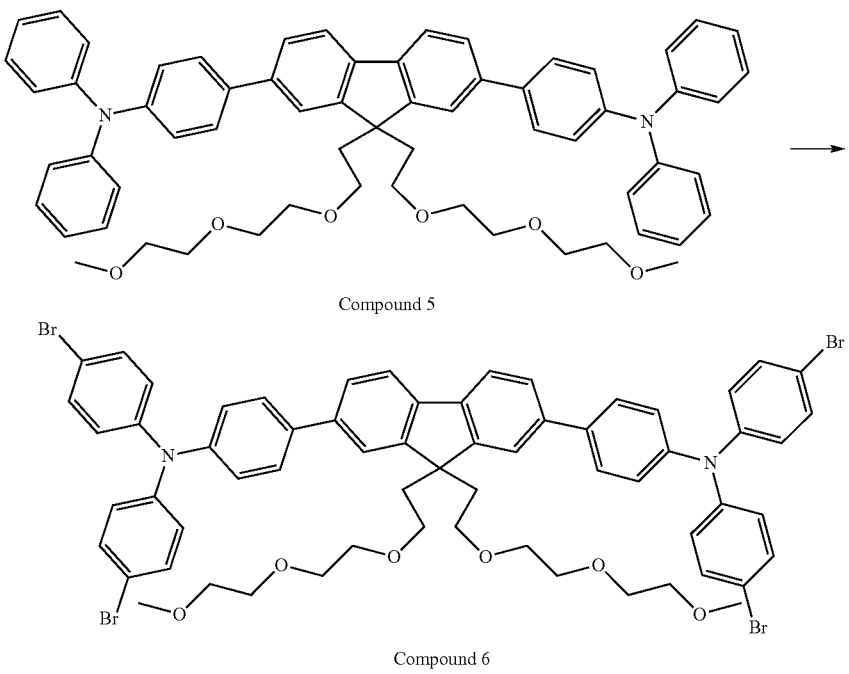

Compound 5

Compound 6

Aside from using Compound 5 instead of Compound 2, synthesis was carried out in the same way as in Synthesis Example 3, giving 7.15 g (yield, 57%; this being the two-step yield from Compound 1) of Compound 6 as a light-yellow solid. The ¹H-NMR and LC/MS results were as follows.

¹H-NMR (300 MHz, CDCl₃):

δ 2.46 (app t, J=7.2 Hz, 4H), 2.84 (app t, J=7.2 Hz, 4H), 3.20-3.24 (m, 4H), 3.30 (s, 6H), 3.37-350 (m, 12H), 7.01 (d, J=9.0 Hz, 8H), 7.15 (d, J=8.4 Hz, 4H), 7.38 (d, J=9.0 Hz, 8H), 7.56-7.61 (m, 8H), 7.73 (d, J=7.8 Hz, 2H).

LC/MS (ESI⁺) m/z; 1278 [M+NH₄]⁺.

[Synthesis Example 7] Synthesis of Compound 7

[Chemical Formula 36]

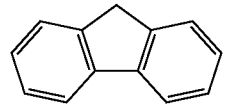

+

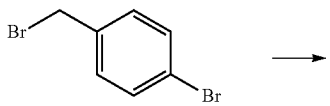

→

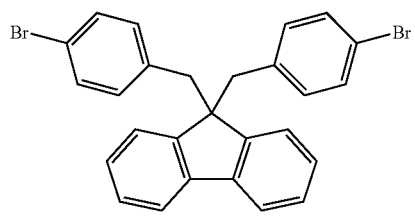

Compound 7 t-BuOK (6.73 g, 60 mmol) was added at room temperature to a THF solution (20 mL) of fluorene (3.32 g, 20 mmol), following which a THF solution (46 mL) of 4-bromobenzyl bromide (11.0 g, 44 mmol) was added dropwise at room temperature and refluxed under heating for 8 hours. Following reaction completion, the system was allowed to cool to room temperature and water (30 mL) was added. The crude product obtained by extracting the organic layer with ethyl acetate, drying over magnesium sulfate and concentration was purified by silica gel column chromatography (eluate, hexane/ethyl acetate (100/1→50/1), giving 7.25 g (yield, 72%) of Compound 7 as a white solid. The ¹H-NMR and MALDI-TOF-MS results were as follows.

¹H-NMR (300 MHz, CDCl₃):

δ 3.31 (s, 4H), 6.48 (d, J=8.4 Hz, 4H), 7.00 (d, J=8.7 Hz, 4H), 7.20-7.31 (m, 4H), 7.39-7.42 (m, 4H).

MALDI-TOF-MS m/z; 526 [M+Na]⁺.

[Synthesis Example 8] Synthesis of Compound 8

[Chemical Formula 37]

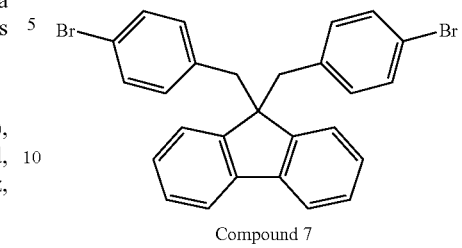

Compound 7

+

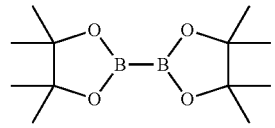

→

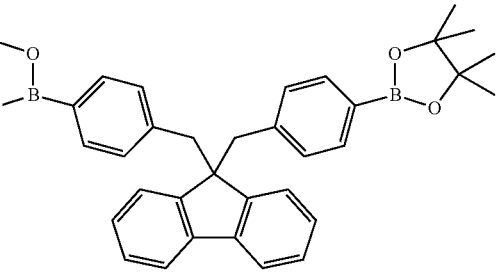

Compound 8

Aside from using Compound 7 instead of 4-bromotriphenylamine, synthesis was carried out in the same way as in Synthesis Example 4, giving 5.86 g (yield, 87%) of Compound 8 as a colorless solid. The ¹H-NMR and LC/MS results were as follows.

¹H-NMR (300 MHz, CDCl₃):

δ 1.27 (s, 24H), 3.34 (s, 4H), 6.68 (d, J=7.8 Hz, 4H), 7.17-7.26 (m, 4H), 7.35-7.41 (m, 8H).

LC/MS (APCI⁺) m/z; 598 [m]⁺.

[Synthesis Example 9] Synthesis of Compound 9

[Chemical Formula 38]

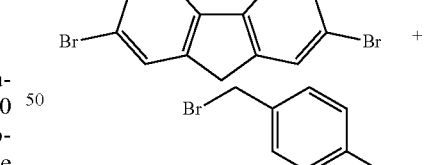

+

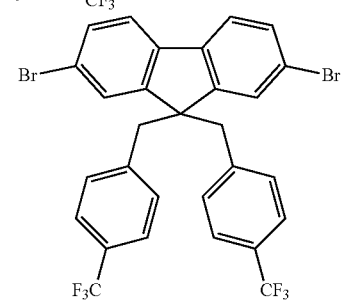

Compound 9

Aside from using 2,7-dibromofluorene instead of fluorene and using 4-trifluoromethylbenzyl bromide instead of 4-bromobenzyl bromide, synthesis was carried out in the same way as in Synthesis Example 7, giving 10.2 g (yield, 80%) of Compound 9 as a colorless solid. The ¹H-NMR results were as follows.

¹H-NMR (300 MHz, CDCl₃):
δ 3.41 (s, 4H), 6.73 (d, J=8.4 Hz, 4H), 7.19-7.22 (m, 6H), 7.38 (dd, J=1.8, 8.4 Hz, 2H), 759 (d, J=1.2 Hz, 2H).

[Synthesis Example 10] Synthesis of Compound 10

[Chemical Formula 39]

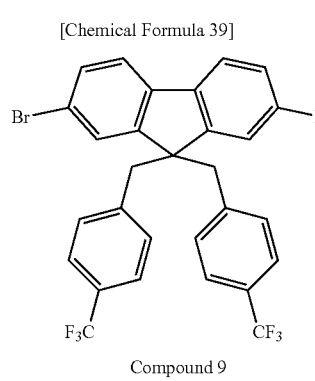

Compound 9

+

[Chemical Formula 40]

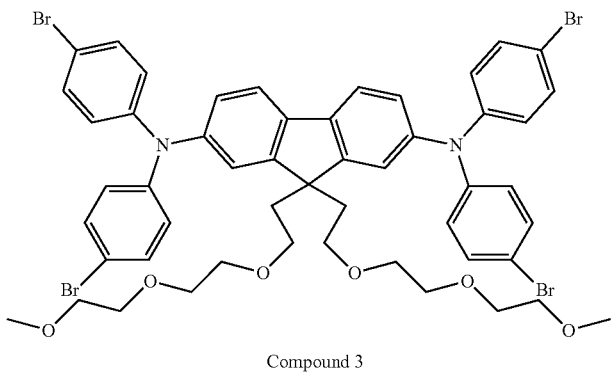

Compound 3

+

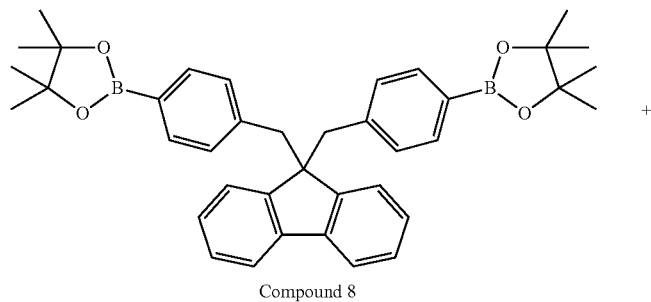

Compound 8

+

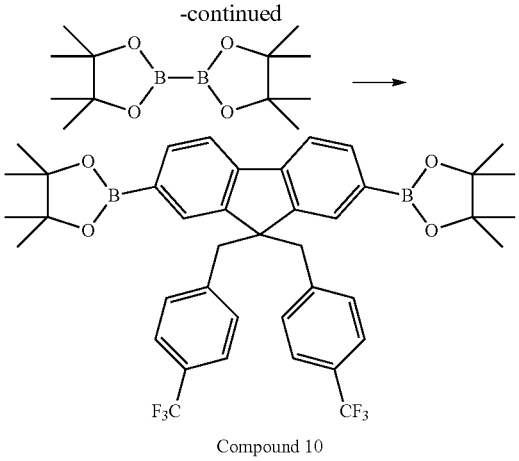

Compound 10

Aside from using Compound 9 instead of 4-bromotriphenylamine, synthesis was carried out in the same way as in Synthesis Example 4, giving 5.60 g (yield, 81%) of Compound 10 as a colorless solid. The ¹H-NMR and LC/MS results were as follows.

¹H-NMR (300 MHz, CDCl₃):
δ 1.41 (s, 24H), 3.45 (s, 4H), 6.71 (d, J=7.8 Hz, 4H), 7.13 (d, J=7.8 Hz, 4H), 7.43 (d, J=7.5 Hz, 2H), 7.70 (d, J=7.8 Hz, 2H), 7.83 (s, 2H).

LC/MS (ESI⁺) m/z; 780[M+HCOO]⁻.

[Synthesis Example 11] Synthesis of Polymer 1

-continued

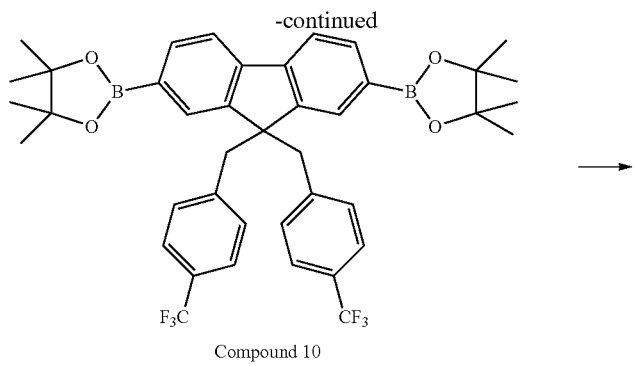

Compound 10

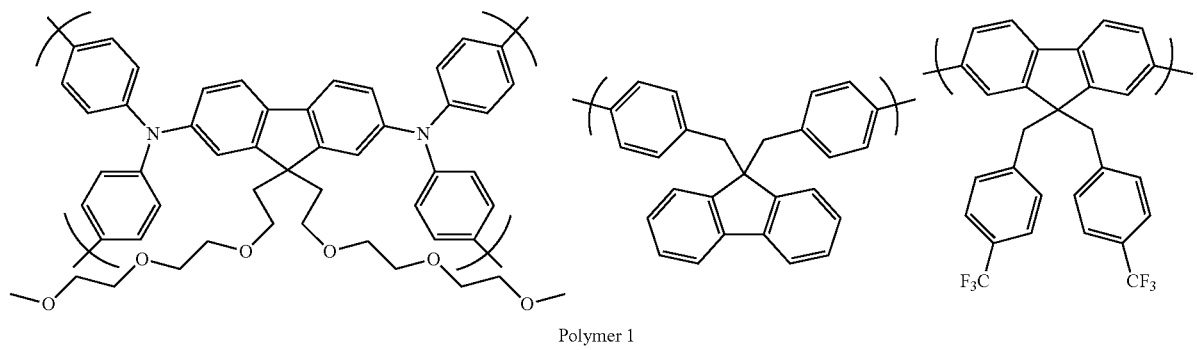

Polymer 1

Methyl tri-n-octylammonium chloride (64.7 mg, 0.16 mmol), Pd(PPh$_3$)$_4$ (3.7 mg, 3.2 µmol) and a 2 mol/L aqueous solution of sodium carbonate (3.2 mL, 6.4 mmol) were added to a toluene solution (18 mL) of Compound 3 synthesized in Synthesis Example 3 (887 mg, 0.8 mmol), Compound 8 synthesized in Synthesis Example 8 (402 mg, 0.67 mmol) and Compound 10 synthesized in Synthesis Example 10 (494 mg, 0.67 mmol), and the system was refluxed under heating for 3 hours. Phenylboronic acid (97.5 mg, 0.8 mmol) was added to the reaction mixture, and the system was refluxed under heating for another 4 hours. Following reaction completion, the organic layer was washed with 1 mol/L hydrochloric acid and subsequently dried over sodium sulfate. The organic layer was Celite filtered, subsequently concentrated to one-fourth the volume and added dropwise to methanol (180 mL). After 1 hour of stirring at room temperature, the solid that deposited out was collected by filtration. This solid was dissolved in toluene (16 mL), the resulting solution was added dropwise to methanol (180 mL), and the mixture was stirred for 1 hour at room temperature, after which the solid that deposited out was collected by filtration, giving 0.90 g of Polymer 1 as a light-green solid. GPC measurement yielded the following results: Mw=14,200, Mn=5,000, and Mw/Mn=2.8.

[Synthesis Example 12] Synthesis of Polymer 2

[Chemical Formula 41]

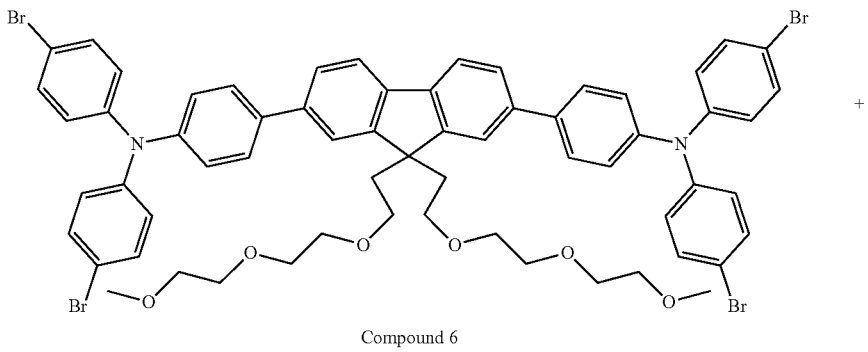

Compound 6

+

-continued

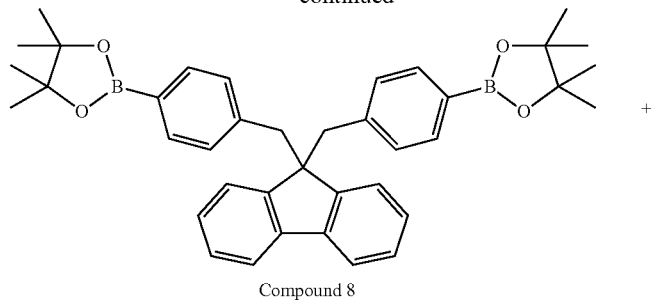

Compound 8

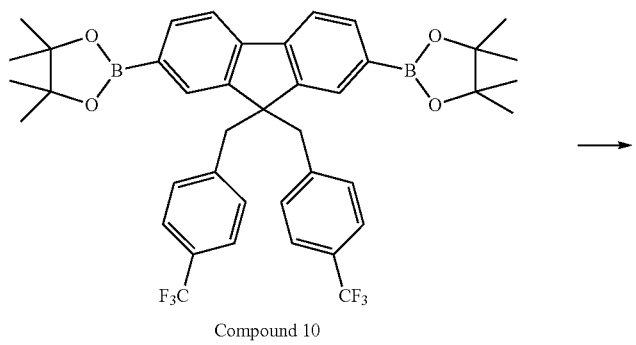

Compound 10

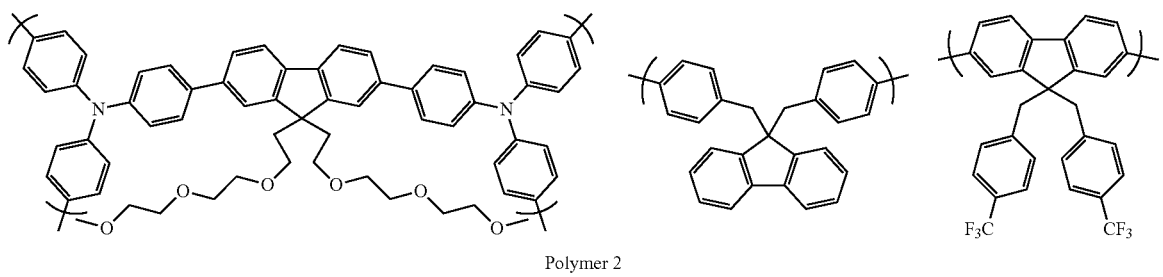

Polymer 2

Aside from using Compound 6 synthesized in Synthesis Example 6 instead of Compound 3, synthesis was carried out in the same way as in Synthesis Example 11, giving 0.66 g of Polymer 2 as a light-yellow solid. GPC measurement yielded the following results: Mw=40,300, Mn=5,000, and Mw/Mn=8.1.

[2] Preparation of Charge-Transporting Varnish

[Working Example 1] Charge-Transporting Varnish A 1,3-Dimethylimidazolidinone (2 g) was added, within a glove box with nitrogen circulation, to a mixture of Polymer 1 (64 mg), Oligoaniline Compound 1 (18 mg) synthesized according to the method described in WO 2013/084664 and phosphotungstic acid (89 mg; Kanto Chemical Co.), and dissolved by stirring under applied heat at 50° C. Cyclohexanol (2 g) was added to this solution and stirring was carried out, giving a green-colored solution. This solution was filtered with a syringe filter having a pore size of 0.2 μm, giving Charge-Transporting Varnish A.

[Chemical Formula 42]

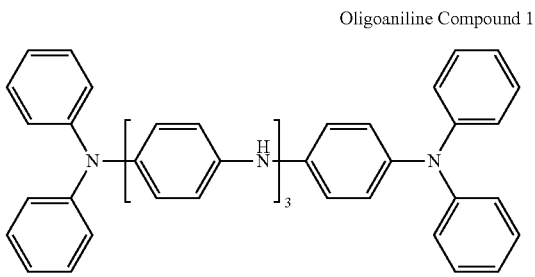

Oligoaniline Compound 1

[Working Example 2] Charge-Transporting Varnish B

Aside from using Polymer 2 instead of Polymer 1, a charge-transporting varnish was prepared by the same method as in Working Example 1.

57

[Comparative Example 1] Charge-Transporting Varnish C

Aside from not using Polymer 1 and setting the amounts in which Oligoaniline Compound 1 and phosphotungstic acid were used to 20 mg and 100 mg, respectively, Charge-Transporting Varnish C was prepared by the same method as in Working Example 1.

[3] Fabrication of Organic EL Devices (OLED Devices) and Evaluation of Device Characteristics A glass substrate with dimensions of 25 mm×25 mm×0.7 mm (t) and having indium-tin oxide (ITO) patterned on the surface to a film thickness of 150 nm (referred to below as the "ITO substrate") was used as the substrate when evaluating the electrical characteristics. Prior to use, impurities on the surface of the ITO substrate were removed with an $O_2$ plasma cleaning system (150 W, 30 seconds).

[Working Example 3] Fabrication of OLED Device Using Charge-Transporting Varnish A Charge-Transporting Varnish A obtained in Working Example 1 was applied to an ITO substrate using a spin coater, then dried at 80° C. for 1 minute and subsequently baked for 15 minutes at 230° C., thereby forming a 30 nm uniform thin film on the ITO substrate.

Next, using a vapor deposition system (degree of vacuum, $1.0 \times 10^{-5}$ Pa), thin films of tris(8-quinolinolate)aluminum (III) ($Alq_3$), lithium fluoride and aluminum were successively deposited on the ITO substrate where the thin film was formed, thereby giving an OLED device. At this time, vapor deposition was carried out at a rate of 0.2 nm/s for $Alq_3$ and aluminum, and at a rate of 0.02 nm/s for lithium fluoride. The film thicknesses were set to, respectively, 40 nm, 0.5 nm and 100 nm.

To prevent the device characteristics from deteriorating due to the influence of oxygen, moisture and the like in air, the OLED device was sealed with sealing substrates, following which the characteristics were evaluated. Sealing was carried out by the following procedure.

In a nitrogen atmosphere having an oxygen concentration of not more than 2 ppm and a dew point of not more than −85° C., the organic EL device was placed between sealing substrates and the sealing substrates were laminated together using an adhesive (XNR5516Z-B1, from Nagase ChemteX Corporation). At this time, a desiccant (HD-071010W-40, from Dynic Corporation) was placed, together with the OLED device, within the sealing substrates.

The laminated sealing substrates were irradiated with UV light (wavelength, 365 nm; dosage, 6,000 mJ/cm$^2$), and then annealed at 80° C. for 1 hour to cure the adhesive.

[Working Example 4] Fabrication of OLD Device Using Charge-Transporting Varnish B Aside from using Charge-Transporting Varnish B obtained in Working Example 2 instead of Charge-Transporting Varnish A, an OLED device was fabricated by the same method as in Working Example 3.

[Comparative Example 2] Fabrication of OLED Device Using Charge-Transporting Varnish C Aside from using Charge-Transporting Varnish C obtained in Comparative Example 1 instead of Charge-Transporting Varnish A, an OLED Device was fabricated by the same method as in Working Example 3.

The electrical characteristics of the OLED devices obtained in Working Examples 3 and 4 and Comparative Example 2 were measured. Table 1 shows the current densities, brightnesses and current efficiencies at a driving voltage of 5V.

TABLE 1

|  | Current density (mA/cm$^2$) | Brightness (cd/m$^2$) | Current efficiency (cd/A) |
| --- | --- | --- | --- |
| Working Example 3 | 95 | 1,360 | 1.4 |
| Working Example 4 | 107 | 2,300 | 2.2 |
| Comparative Example 2 | 3,425 | 611 | 0.0 |

Table 1 shows that, in Comparative Example 2 which used Charge-Transporting Varnish C wherein neither Polymer 1 nor Polymer 2 was added, the current efficiency was markedly lower and the brightness with respect to the current density was lower than the results obtained in Working Examples 3 and 4.

The invention claimed is:
1. A fluorine atom-containing polymer which is a condensation polymer of a fluorene derivative that provides recurring units of formula (1) below, a fluorene derivative that provides recurring units of formula (2) below and a fluorene derivative that provides recurring units of formula (3) below

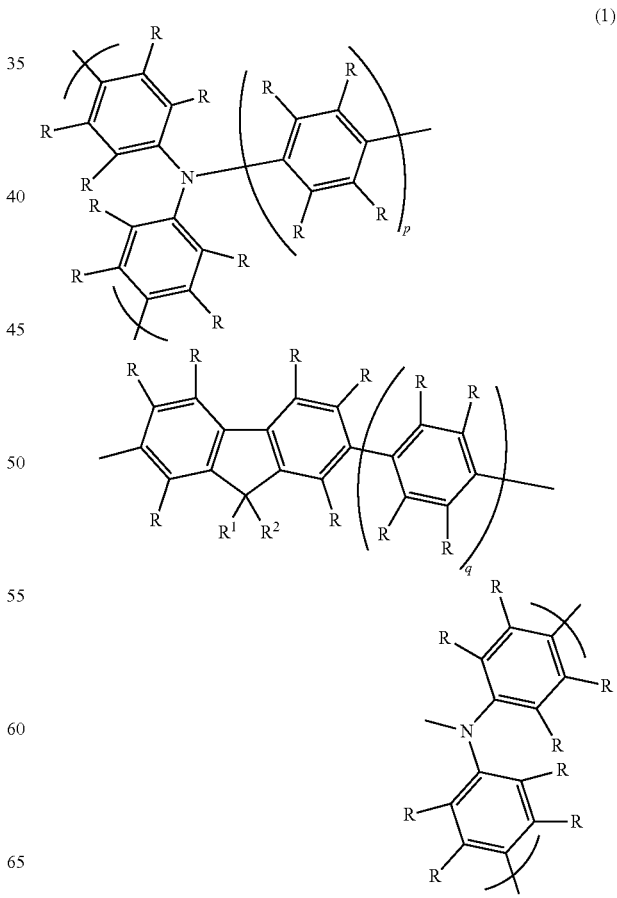

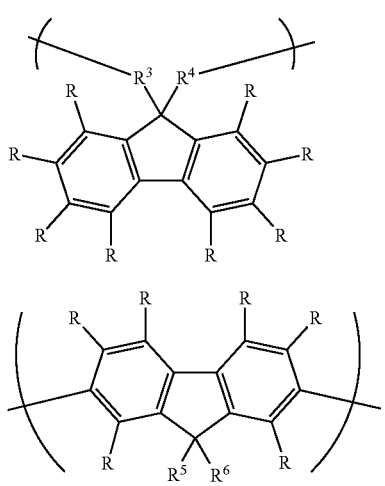

wherein
- $R^1$ and $R^2$ are each independently a hydrogen atom, an alkyl group of 1 to 20 carbon atoms, an alkenyl group of 2 to 20 carbon atoms, an alkynyl group of 2 to 20 carbon atoms, an aryl group of 6 to 20 carbon atoms, a heteroaryl group of 2 to 20 carbon atoms, an alkoxy group of 1 to 20 carbon atoms, an alkenyloxy group of 2 to 20 carbon atoms, an alkynyloxy group of 2 to 20 carbon atoms, an aryloxy group of 6 to 20 carbon atoms, a heteroaryloxy group of 2 to 20 carbon atoms or an alkyl group of 2 to 20 carbon atoms which includes at least one ether structure, with the proviso that at least one of $R^1$ and $R^2$ is said alkyl group, alkoxy group, alkenyloxy group, alkynyloxy group, aryloxy group, heteroaryloxy group, or alkyl group which includes at least one ether structure;
- $R^3$ and $R^4$ are each independently a nonconjugated divalent organic group;
- $R^5$ is a hydrogen atom, or an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom may be substituted with a fluorine atom;
- $R^6$ is an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom is substituted with a fluorine atom;
- each R is independently a hydrogen atom, a halogen atom, a nitro group, a cyano group, an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms or alkynyloxy group of 2 to 20 carbon atoms which may be substituted with $Z^1$, or an aryl group of 6 to 20 carbon atoms, heteroaryl group of 2 to 20 carbon atoms, aryloxy group of 6 to 20 carbon atoms or heteroaryloxy group of 2 to 20 carbon atoms which may be substituted with $Z^2$;
- $Z^1$ is a halogen atom, a nitro group, a cyano group, or an aryl group of 6 to 20 carbon atoms, heteroaryl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms or heteroaryl group of 2 to 20 carbon atoms which may be substituted with $Z^3$;
- $Z^2$ is a halogen atom, a nitro group, a cyano group, or an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms or heteroaryl group of 2 to 20 carbon atoms which may be substituted with $Z^3$;
- $Z^3$ is a halogen atom, a nitro group or a cyano group; and
- p and q are each independently 0 or 1.

2. The polymer of claim 1, wherein the weight-average molecular weight is from 1,000 to 200,000.

3. The polymer of claim 1, wherein $R^1$ and $R^2$ are both alkyl groups of 1 to 20 carbon atoms or both alkyl groups of 2 to 20 carbon atoms which include at least one ether structure.

4. The polymer of claim 1, wherein $R^3$ and $R^4$ are each —$R^c$—Ar— wherein $R^c$ is an alkylene group of 1 to 20 carbon atoms, and Ar is an arylene group of 6 to 20 carbon atoms.

5. The polymer of claim 1, wherein $R^5$ is an alkyl group of 1 to 20 carbon atoms, alkenyl group of 2 to 20 carbon atoms, alkynyl group of 2 to 20 carbon atoms, alkoxy group of 1 to 20 carbon atoms, alkenyloxy group of 2 to 20 carbon atoms, alkynyloxy group of 2 to 20 carbon atoms, aryl group of 6 to 20 carbon atoms, aralkyl group of 7 to 20 carbon atoms, alkylaralkyl group of 8 to 20 carbon atoms, heteroaryl group of 2 to 20 carbon atoms, aryloxy group of 6 to 20 carbon atoms or heteroaryloxy group of 2 to 20 carbon atoms in which at least one hydrogen atom is substituted with a fluorine atom.

6. A charge-transporting substance consisting of the polymer of claim 1.

7. A charge-transporting varnish comprising the charge-transporting substance of claim 6, a charge-transporting substance that contains no fluorine atoms, a dopant consisting of a heteropolyacid, and an organic solvent.

8. The charge-transporting varnish of claim 7, wherein the charge-transporting substance that contains no fluorine atoms is an aniline derivative.

9. A charge-transporting thin film produced using the charge-transporting varnish of claim 7.

10. An electronic device comprising the charge-transporting thin film of claim 9.

11. An organic electroluminescent device comprising the charge-transporting thin film of claim 9.

12. A method for producing a charge-transporting thin film, comprising the steps of applying the charge-transporting varnish of claim 7 to a substrate and evaporating off the solvent.

13. A method for producing the fluorine atom-containing polymer of claim 1, comprising the step of condensation polymerizing a fluorene derivative of formula (1') below, a fluorene derivative of formula (2') below and a fluorene derivative of formula (3') below

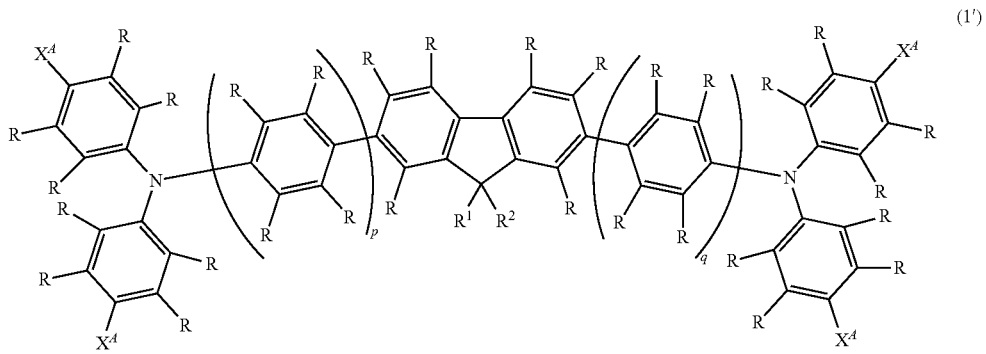

(1')

(2')

(3')

wherein $R^1$ to $R^6$, R, p and q are as defined above; each $X^A$ is independently a halogen atom or a pseudo-halogen group; and each $X^B$ is independently a group of formula (4) or (5) below

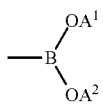

(4)

-continued

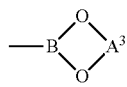

(5)

wherein $A^1$ and $A^2$ are each independently a hydrogen atom, an alkyl group of 1 to 20 carbon atoms or an aryl group of 6 to 20 carbon atoms; and $A^3$ is an alkanediyl group of 1 to 20 carbon atoms or an arylene group of 6 to 20 carbon atoms.

14. A fluorene derivative of the following formula

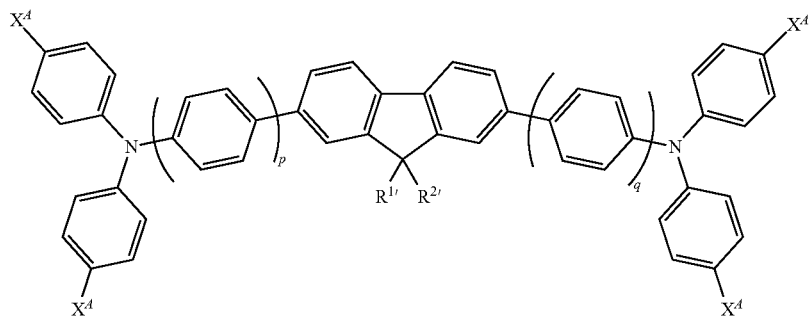

wherein $R^{1'}$ and $R^{2'}$ are alkyl groups of 2 to 20 carbon atoms which include at least one ether structure; each $X^A$ is independently a halogen atom or a pseudo-halogen group; and p and q are each independently 0 or 1.

15. A fluorene derivative of the following formula

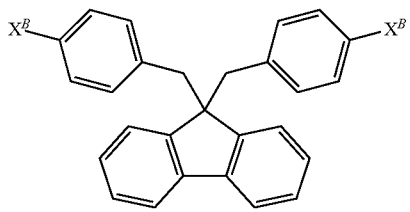

wherein each $X^B$ is independently a group of formula (4) or (5) below

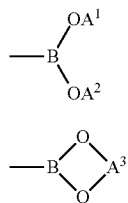 (4)

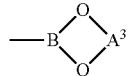 (5)

wherein $A^1$ and $A^2$ are each independently a hydrogen atom, an alkyl group of 1 to 20 carbon atoms or an aryl group of 6 to 20 carbon atoms; and $A^3$ is an alkanediyl group of 1 to 20 carbon atoms or an arylene group of 6 to 20 carbon atoms.

16. A fluorene derivative of the following formula

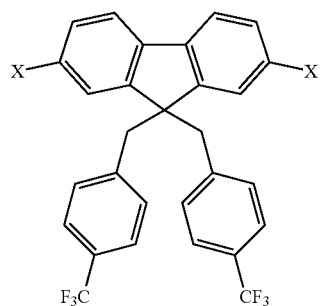

wherein each X is independently a halogen atom, a pseudo-halogen group, or a group of formula (4) or (5) below

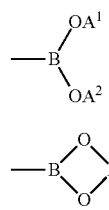 (4)

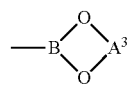 (5)

wherein $A^1$ and $A^2$ are each independently a hydrogen atom, an alkyl group of 1 to 20 carbon atoms or an aryl group of 6 to 20 carbon atoms; and $A^3$ is an alkanediyl group of 1 to 20 carbon atoms or an arylene group of 6 to 20 carbon atoms.

* * * * *